US011345965B2

(12) United States Patent
McCord et al.

(10) Patent No.: US 11,345,965 B2
(45) Date of Patent: May 31, 2022

(54) MATERIALS AND METHODS FOR MULTIPLEX DETECTION OF BODY FLUIDS

(71) Applicants: Bruce McCord, Miami, FL (US); Quentin Gauthier, Miami, FL (US); Sohee Cho, Miami, FL (US)

(72) Inventors: Bruce McCord, Miami, FL (US); Quentin Gauthier, Miami, FL (US); Sohee Cho, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/104,273

(22) Filed: Nov. 25, 2020

(65) Prior Publication Data

US 2021/0102254 A1    Apr. 8, 2021

Related U.S. Application Data

(63) Continuation of application No. 16/456,423, filed on Jun. 28, 2019.

(60) Provisional application No. 62/695,482, filed on Jul. 9, 2018.

(51) Int. Cl.
| | |
|---|---|
| *C07H 21/04* | (2006.01) |
| *C12Q 1/68* | (2018.01) |
| *C12Q 1/6883* | (2018.01) |
| *G01N 33/53* | (2006.01) |
| *C12Q 1/6827* | (2018.01) |
| *C12Q 1/686* | (2018.01) |

(52) U.S. Cl.
CPC .......... *C12Q 1/6883* (2013.01); *C12Q 1/686* (2013.01); *C12Q 1/6827* (2013.01); *G01N 33/53* (2013.01); *C12Q 2600/118* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | |
|---|---|---|
| 10,053,740 B1 | 8/2018 | McCord et al. |
| 10,619,218 B2 | 4/2020 | McCord et al. |

FOREIGN PATENT DOCUMENTS

KR    101498640 B1    3/2015

OTHER PUBLICATIONS

Silva et al. (Forensic Science International: Genetics, vol. 23, pp. 55-63, Feb. 1, 2016) (Year: 2016).*
Antunes (Dissertation: The study of tissue-specific DNA methylation as a method for the epigenetic discrimination of forensic samples, Nov. 21, 2017). (Year: 2017).*
Forensic body fluid identification using epigenetic markers based on multiplex PCR and pyrosequncing by Sohee Cho, 2017-2018 (Year: 2017).*
Forensic applications of epigenetics Power point presentation authored by Sohee Cho and Bruce McCord (Year: 2018).*
An, J.H. et al., "DNA methylation-specific multiplex assays for body fluid identification," Int J Legal Med., 2013, vol. 127(1), pp. 35-43, 2013, doi:10.1007/s00414-012-0719-1.
Antunes, J. et al., "High-resolution melt analysis of DNA methylation to discriminate semen in biological stains," Anal. Biochem., vol. 494: (2016), pp. 40-45.
Antunes, J., "The Study of Tissue-Specific DNA Methylation as a Method for the Epigenetic Discrimination of Forensic Samples." FIU Electronic Thesis and Dissertations, 2017, 3676, pp. 1-246.
Bocklandt, Sven, "Epigenetic predictor of age," PLoS One, vol. 6, Issue 6, pp. 1-6 (e14821), Jun. 2011.
Boks, Marco P. et al., The Relationship of DNA Methylation with Age, Gender and Genotype in Twins and Healthy Controls, PLoS One, vol. 4, Issue 8, p. 1-8 (e6767), 2009.
Brait, Mariana and Sidransky, David, "Cancer epigenetics: above and beyond," Toxicol Mech Methods. vol. 21, Issue 4, pp. 275-288, May 2011.
Forat, Sophia et al., "Methylation Markers for the Identification of Body Fluids and Tissues from Forensic Trace Evidence," PLoS One, Feb. 1, 2016, 11(2):e0147973. doi: 10.1371/journal.pone. 0147973.
Gauthier, Q.T. et al., "Development of a body fluid identification multiplex via DNA methylation analysis." Electrophoresis 1-10, 2019.
Kayser, Manfred and Knijff, Peter De, "Improving human forensics through advances in genetics, genomics and molecular biology," Nature Reviews Genetics, vol. 12, pp. 179-192, Mar. 2011.
Lieb, Jason D. et al., "Applying Whole-Genome Studies of Epigenetic Regulation to Study Human Disease," Cytogenet Genome Res., vol. 114, Issue (1), pp. 1-15, 2006.
Madi, Tania et al., "The determination of tissue-specific DNA methylation patterns in forensic biofluids using bisulfite modification and pyrosequencing," Electrophoresis, vol. 33, Issue12, pp. 1736-1745, 2012.

(Continued)

*Primary Examiner* — Jeanine A Goldberg
(74) *Attorney, Agent, or Firm* — Saliwanchik, Lloyd & Eisenschenk

(57) ABSTRACT

The invention pertains to analyzing the levels of DNA methylation at specific genetic loci to detect specific body fluids, for example, vaginal secretions or vaginal epithelial cells, semen or sperms, saliva or buccal epithelial cells, or blood or blood cells. Particularly, the levels of methylation of DNA at the genetic loci corresponding to SEQ ID NOs: 1, 6, 11, and 16, more particularly, SEQ ID NOs: 25, 26, 27, and 28, are used to detect vaginal secretions or vaginal epithelial cells, semen or sperms, saliva or buccal epithelial cells, and blood or blood cells, respectively. The level of methylation at the specific loci can be determined by sequencing of the amplicons produced using specific primers designed to amplify the specific loci. Kits containing the primers and reagents for carrying out the methods disclosed herein are also provided.

18 Claims, 9 Drawing Sheets

Specification includes a Sequence Listing.

(56) References Cited

OTHER PUBLICATIONS

McCord et al., Forensic DNA Analysis, Analytical Chemistry, 2019, 91 (1), p. 673-688.

Silva, Deborah S.B.S. et al., "Developmental validation of studies of epigenetic DNA methylation markers for the detection of blood, semen, and saliva samples," Forensic Science International: Genetics, 2016, vol. 23, pp. 55-63.

Weidner Carola Ingrid et al., "Aging of blood can be tracked by DNA Methylation changes at just three CpG sites," Genome biology, vol. 15, Issue 2, pp. 1-12, 2014.

Zbiec-Piekarska, Renata et al., "Development of a forensically useful age prediction method based on DNA methylation analysis" Forensic Sci. Int. Genet., vol. 17, pp. 173-179, 2015.

* cited by examiner

SEQUENCE LISTING

```
<160> NUMBER OF SEQ ID NOS: 28

<210> SEQ ID NO 1
<211> LENGTH: 131
<212> TYPE: DNA
<213> ORGANISM: Homo sapiens

<400> SEQUENCE: 1
tcaaatcagg gtgtgggcag agctgtgctc cctctggacg ccttttccct cttccagcat      60
ctgttggctg ctggcgcccc ttggcacgtg gtgcatcgct ccagtctggg ctctgtcttc     120
ctggcatgct c                                                          131

<210> SEQ ID NO 2
<211> LENGTH: 25
<212> TYPE: DNA
<213> ORGANISM: Artificial sequence
<220> FEATURE:
<223> OTHER INFORMATION: primer

<400> SEQUENCE: 2
gttttaaatt agggtgtggg tagag                                            25

<210> SEQ ID NO 3
<211> LENGTH: 27
<212> TYPE: DNA
<213> ORGANISM: Artificial sequence
<220> FEATURE:
<223> OTHER INFORMATION: primer

<400> SEQUENCE: 3
cataccaaaa aaacaaaacc caaacta                                          27

<210> SEQ ID NO 4
<211> LENGTH: 131
<212> TYPE: DNA
<213> ORGANISM: Artificial sequence
<220> FEATURE:
<223> OTHER INFORMATION: Sequence of the locus specific for vaginal
      epithelial cell after bisulfite treatment assuming 100%
      unmethylation of all CpG sites

<400> SEQUENCE: 4
ttaaattagg gtgtgggtag agttgtgttt tttttggatg tttttttttt tttttagtat      60
ttgttggttg ttggtgtttt tggtatgtg gtgtattgtt ttagtttggg ttttgttttt     120
ttggtatgtt t                                                          131

<210> SEQ ID NO 5
<211> LENGTH: 131
<212> TYPE: DNA
<213> ORGANISM: Homo sapiens
```

<400> SEQUENCE: 5
tcaaatcagg gtgtgggcag agctgtgctc cctctggacg ccttttccct cttccagcat    60
ctgttggctg ctggcgcccc ttggcacgtg gtgcatcgct ccagtctggg ctctgtcttc   120
ctggcatgct c                                                        131

<210> SEQ ID NO 6
<211> LENGTH: 91
<212> TYPE: DNA
<213> ORGANISM: Homo sapiens

<400> SEQUENCE: 6
gggtgagggc ccaagggcac cgcccctgag aaccacccc aacgcgaggc cacccgcttc     60
ccgggccggt cagatgaggt tttgagggga g                                   91

<210> SEQ ID NO 7
<211> LENGTH: 18
<212> TYPE: DNA
<213> ORGANISM: Artificial sequence
<220> FEATURE:
<223> OTHER INFORMATION: primer

<400> SEQUENCE: 7
gggtgagggt ttaagggt                                                  18

<210> SEQ ID NO 8
<211> LENGTH: 18
<212> TYPE: DNA
<213> ORGANISM: Artificial sequence
<220> FEATURE:
<223> OTHER INFORMATION: primer

<400> SEQUENCE: 8
ctcccctcaa aacctcat                                                  18

<210> SEQ ID NO 9
<211> LENGTH: 91
<212> TYPE: DNA
<213> ORGANISM: Artificial sequence
<220> FEATURE:
<223> OTHER INFORMATION: Sequence of the locus specific for sperm after
      bisulfite treatment assuming 100% unmethylation of all CpG sites

<400> SEQUENCE: 9
gggtgagggt ttaagggtat tgttttgag aattattttt aatgtgaggt tatttgtttt    60
ttgggttggt tagatgaggt tttgagggga g                                   91

<210> SEQ ID NO 10
<211> LENGTH: 91
<212> TYPE: DNA
<213> ORGANISM: Homo sapiens

<400> SEQUENCE: 10
gggtgagggc ccaagggcac cgcccctgag aaccacccc aacgcgaggc cacccgcttc     60
ccgggccggt cagatgaggt tttgagggga g                                   91

<210> SEQ ID NO 11
<211> LENGTH: 210
<212> TYPE: DNA
<213> ORGANISM: Homo sapiens

<400> SEQUENCE: 11

```
agcaggggcc caggccatgc cactgttgca aatctgagg gcggcatacc ggcaagcctg    60
agcagttgcc acggcctcag ccccacgggc accgccagga agaaaaatg caacttactc   120 ctgggcaccg gacaaccgg tggaacctca ggcgtgggac ggctgccgga aagcagggcc   180
caatcagaga cagctgcctt gctgtgtggc                                   210
```

<210> SEQ ID NO 12
<211> LENGTH: 26
<212> TYPE: DNA
<213> ORGANISM: Artificial sequence
<220> FEATURE:
<223> OTHER INFORMATION: primer

<400> SEQUENCE: 12

```
agtaggggtt taggttatgt tattgt                                        26
```

<210> SEQ ID NO 13
<211> LENGTH: 24
<212> TYPE: DNA
<213> ORGANISM: Artificial sequence
<220> FEATURE:
<223> OTHER INFORMATION: primer

<400> SEQUENCE: 13

```
accacacaac aaaacaacta tctc                                          24
```

<210> SEQ ID NO 14
<211> LENGTH: 210
<212> TYPE: DNA
<213> ORGANISM: Artificial sequence
<220> FEATURE:
<223> OTHER INFORMATION: Sequence of the locus specific for blood cells
     after bisulfite treatment assuming 100% unmethylation of all CpG
     sites

<400> SEQUENCE: 14

```
agtaggggtt taggttatgt tattgttgta aaatttgagg gtggtatatt ggtaagtttg    60
agtagttgtt atggttttag ttttatgggt attgttagga agaaaaatg taatttattt   120 ttgggtattg ggataattgg tgaattttta ggtgtgggat ggttgttgga aagtaggggtt  180 taattagaga tagttgtttt gttgtgtggt                                   210
```

<210> SEQ ID NO 15
<211> LENGTH: 210
<212> TYPE: DNA
<213> ORGANISM: Homo sapiens

<400> SEQUENCE: 15

```
agcaggggcc caggccatgc cactgttgca aaatctgagg gcggcatacc ggcaagcctg    60
agcagttgcc acggcctcag ccccacgggc accgccagga agaaaaatg caacttactc   120 ctgggcaccg gacaaccgg tggaacctca ggcgtgggac ggctgccgga aagcagggcc   180
caatcagaga cagctgcctt gctgtgtggc                                   210
```

<210> SEQ ID NO 16
<211> LENGTH: 158
<212> TYPE: DNA
<213> ORGANISM: Homo sapiens

<400> SEQUENCE: 16

```
agtgggtgcg gttgtgaaat gtagtgcgct caatagtttc ctggtgaagt ttatttttaaa   60 atccgcaccg aagaggaaga cgaggaccgt cacactcggc cttccctaaa ttccaggacc   120
```
ctccgcccga tgcaaactag atgctttagt aggatggg        158

<210> SEQ ID NO 17
<211> LENGTH: 22
<212> TYPE: DNA
<213> ORGANISM: Artificial sequence
<220> FEATURE:
<223> OTHER INFORMATION: primer

<400> SEQUENCE: 17
agtgggtgag gttgtgaaat gt        22

<210> SEQ ID NO 18
<211> LENGTH: 24
<212> TYPE: DNA
<213> ORGANISM: Artificial sequence
<220> FEATURE:
<223> OTHER INFORMATION: primer

<400> SEQUENCE: 18
cccatcctac taaaacatct aatt        24

<210> SEQ ID NO 19
<211> LENGTH: 158
<212> TYPE: DNA
<213> ORGANISM: Artificial sequence
<220> FEATURE:
<223> OTHER INFORMATION: Sequence of the locus specific for buccal
      epithelial cells after bisulfite treatment assuming 100%
      unmethylation of all CpG sites

<400> SEQUENCE: 19
agtgggtgtg gttgtgaaat gtagtgtgtt taatagtttt ttggtgaagt ttatttaaa        60 atttgtattg aagaggaaga tgaggattgt tatatttggt ttttttaaa ttttaggatt        120 ttttgtttga tgtaaattag atgttttagt aggatggg        158

<210> SEQ ID NO 20
<211> LENGTH: 158
<212> TYPE: DNA
<213> ORGANISM: Homo sapiens

<400> SEQUENCE: 20
agtgggtgcg gttgtgaaat gtagtgcgct caatagtttc ctggtgaagt ttatttaaa        60 atccgcaccg aagaggaaga cgaggaccgt cacactcggc cttccctaaa ttccaggacc        120
ctccgcccga tgcaaactag atgctttagt aggatggg        158

<210> SEQ ID NO 21
<211> LENGTH: 17
<212> TYPE: DNA
<213> ORGANISM: Artificial sequence
<220> FEATURE:
<223> OTHER INFORMATION: primer

<400> SEQUENCE: 21
tgtgggtaga gttgtgt        17

<210> SEQ ID NO 22
<211> LENGTH: 21
<212> TYPE: DNA
<213> ORGANISM: Artificial sequence
<220> FEATURE:
<223> OTHER INFORMATION: primer

<400> SEQUENCE: 22
gtttttgaga attattttta a                                                    21

<210> SEQ ID NO 23
<211> LENGTH: 24
<212> TYPE: DNA
<213> ORGANISM: Artificial sequence
<220> FEATURE:
<223> OTHER INFORMATION: primer

<400> SEQUENCE: 23
gttaggaaag aaaaatgtaa ttta                                                 24

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
agtttaatag tttttttggtg                                                     20

<210> SEQ ID NO 25
<211> LENGTH: 60
<212> TYPE: DNA
<213> ORGANISM: Artificial sequence
<220> FEATURE:
<223> OTHER INFORMATION: sequence of the locus specific for vaginal
      epithelial cells after bisulfite treatment assuming 100%
      unmethylation of all CpG sites

<400> SEQUENCE: 25 tgttttttttt tttttttagt atttgttggt tgttggtgtt ttttggtatg tggtgtattg          60

<210> SEQ ID NO 26
<211> LENGTH: 26
<212> TYPE: DNA
<213> ORGANISM: Artificial sequence
<220> FEATURE:
<223> OTHER INFORMATION: sequence of the locus specific for sperms after
      bisulfite treatment assuming 100% unmethylation of all CpG sites

<400> SEQUENCE: 26
tgtgaggtta tttgtttttt gggttg                                               26

<210> SEQ ID NO 27
<211> LENGTH: 40
<212> TYPE: DNA
<213> ORGANISM: Artificial sequence
<220> FEATURE:
<223> OTHER INFORMATION: sequence of the locus specific for blood cells
      after bisulfite treatment assuming 100% unmethylation of all CpG
      sites

<400> SEQUENCE: 27
tgggataatt ggtggaattt taggtgtggg atggttgttg                                40

<210> SEQ ID NO 28
<211> LENGTH: 26
<212> TYPE: DNA
<213> ORGANISM: Artificial sequence
<220> FEATURE:
<223> OTHER INFORMATION: sequence of the locus specific for buccal
      epithelial cells after bisulfite treatment assuming 100%
      unmethylation of all CpG sites

```
<400> SEQUENCE: 28
tgtattgaag aggaagatga ggattg                                                    26
```

MATERIALS AND METHODS FOR MULTIPLEX DETECTION OF BODY FLUIDS

CROSS-REFERENCE TO A RELATED APPLICATION

This application is a continuation application of co-pending application Ser. No. 16/456,423, filed Jun. 28, 2019; which claims the benefit of U.S. provisional application Ser. No. 62/695,482, filed Jul. 9, 2018, both of which are incorporated herein by reference in its entirety.

GOVERNMENT SUPPORT

This invention was made with government support under 2017-NE-BX-0001 awarded by National Institute of Justice. The government has certain rights in the invention.

The Sequence Listing for this application is labeled "SeqList-20Jun19-ST25," which was created on Jun. 20, 2019, and is 8 KB. The Sequence Listing is incorporated herein by reference in its entirety.

BACKGROUND OF THE INVENTION

DNA is used to match a sample retrieved from a crime scene with DNA retrieved from a suspect to identify a connection of the suspect to the crime scene. Current DNA analyses do not permit identifying the source of DNA from a suspect. However, certain forensic cases, such as sexual abuse require confirmation that a DNA from a suspect is from an intimate body fluid.

Techniques currently used for body fluid identification are not based on DNA analysis. For example, microscopic observation of sperms is used to identify semen as a source body fluid or histological staining of glycogen-rich cells is used to identify vaginal cells. However, these tests are only presumptive. For example, if the male donor does not produce sperm, the source cannot be identified as semen. Similarly, false negatives can occur because the glycogen content of vaginal cells varies depending on the menstrual cycle and reproductive age; whereas, false positives can occur because buccal and urogenital skin cells (even from males) can have high glycogen.

Certain other methods are based on protein/enzyme reactivity or cell staining and are merely presumptive. These methods may have low sensitivity and render the portion of the sample useless for subsequent analysis. Therefore, forensic laboratories may be left to choose between isolating DNA to compare a suspect's DNA or determining body fluid of origin.

Certain other methods of identifying source body fluid are based on analyzing RNA transcripts. However, the need to identify a body fluid often arises after DNA is isolated. To perform an RNA transcript analysis, the laboratory technician would have to retrieve a new portion of the original sample (if available) and isolate RNA. However, the original sample may have already been consumed.

BRIEF SUMMARY OF THE INVENTION

The invention provides methods that avoid the problems and difficulties with current methods of detecting body fluids in a sample, particularly, a forensic sample. The methods of the invention depend on the analyses of levels of DNA methylation at specific genetic loci to detect specific body fluids.

In one embodiment, the body fluid and/or cells present in the sample comprise vaginal secretion or vaginal epithelial cell, semen or sperm, saliva or buccal epithelial cell, and blood or blood cell.

An embodiment of the invention provides an assay for determining the presence of one or more body fluids and/or cells present in the sample. Particularly, the assay of the invention can be used to determine the presence of one or more body fluids and/or one or more cells present in the sample, wherein the one or more body fluids and/or cells are selected from vaginal secretion or vaginal epithelial cell, semen or sperm, saliva or buccal epithelial cell, and blood or blood cell.

Another embodiment of the invention provides a multiplex assay for determining the presence of two or more body fluids and/or cells present in the sample. Particularly, the multiplex assay of the invention can be used to determine the presence of two or more body fluids and/or two or more cells present in the sample, wherein the two or more body fluids and/or cells are selected from vaginal secretion or vaginal epithelial cell, semen or sperm, saliva or buccal epithelial cell, and blood or blood cell.

The level of methylation at specific loci in the genomic DNA isolated from a sample can be determined by sequencing of amplicons produced using specific primers designed to amplify the specific loci.

A further embodiment of the invention provides a method for determining the level of methylation at specific loci in the genomic DNA isolated from a cell, for example, a cell suspected to be a vaginal epithelial cell, buccal epithelial cell, sperm, or blood cell isolated from a forensic sample.

Kits containing primers and reagents for carrying out the methods disclosed herein are also provided.

Assays for determining the level of methylation at specific loci in the genomic DNA isolated from a sample are also provided. In certain embodiments, the assays comprise sequencing of amplicons produced using specific primers designed to amplify specific loci in the genomic DNA.

BRIEF DESCRIPTION OF SEQUENCES

Figure 1:
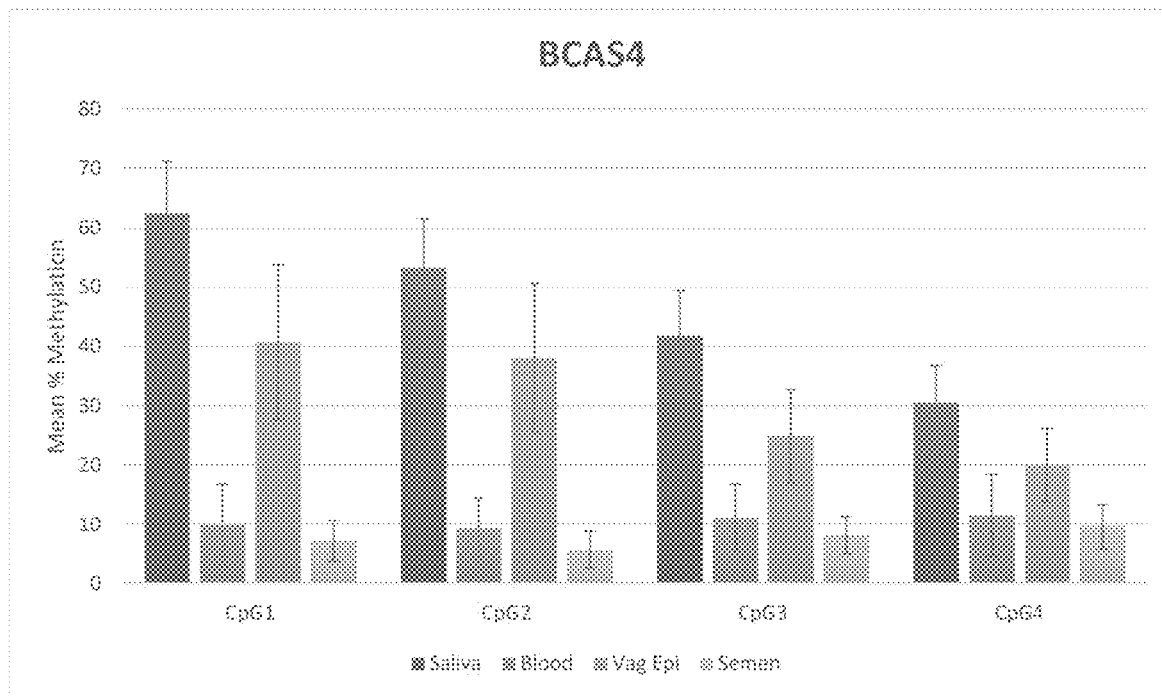
FIG. 1 provides a graph showing the mean percentage methylation of several CpGs found in the markers used for buccal epithelial cells identification. The locus BCAS4 can be used to differentiate buccal epithelial cells from blood and sperm. When considered with the VE_8 marker, which is specific for vaginal epithelial cells, the percentage methylation of several CpGs found in the locus BCAS4 can be used to identify buccal epithelial cells from blood, vaginal epithelial cells, and sperm.
Figure 2:
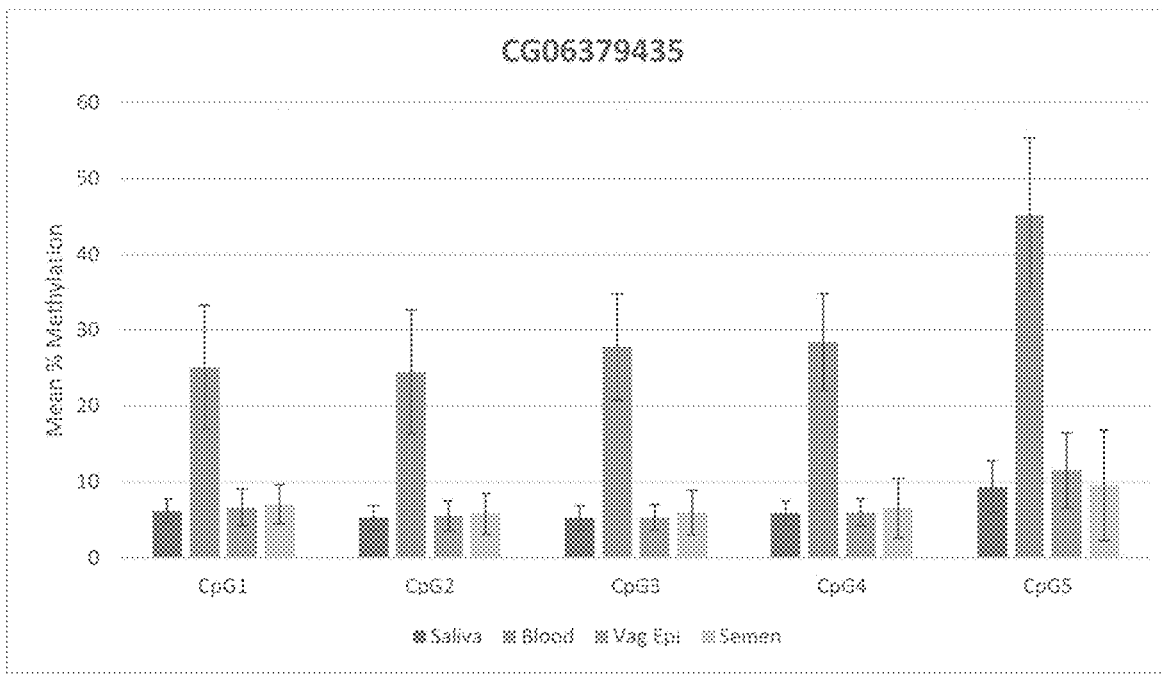
FIG. 2 provides a graph showing the mean percentage methylation of several CpGs found in the markers used for blood identification. CG06379435 can be used to differentiate blood from buccal epithelial cells, vaginal epithelial cells, and sperm.
Figure 3:
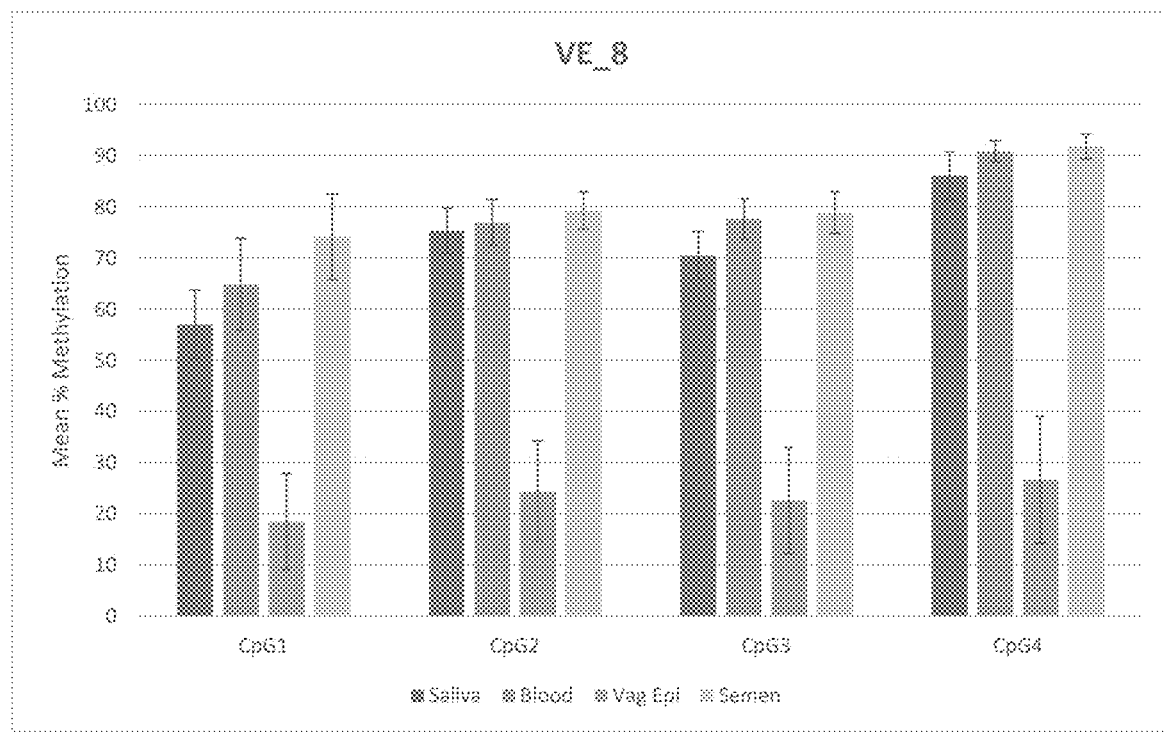
FIG. 3 provides a graph showing the mean percentage methylation of several CpGs found in the markers used for vaginal epithelial cells identification. VE_8 can be used to differentiate vaginal epithelial cells from buccal epithelial cells, blood, and sperm.
Figure 4:
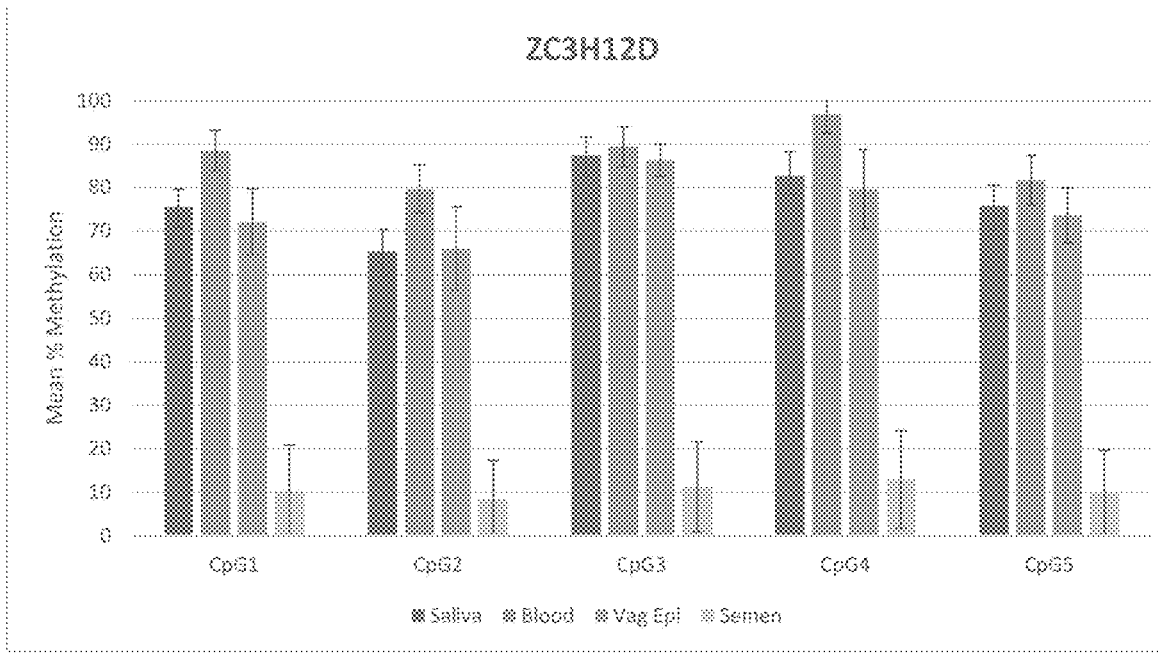
FIG. 4 provides a graph showing the mean percentage methylation of several CpGs found in the markers used for sperm identification. ZC3H12D can be used to differentiate sperm from buccal epithelial cells, blood, and vaginal epithelial cells.
Figure 5A:
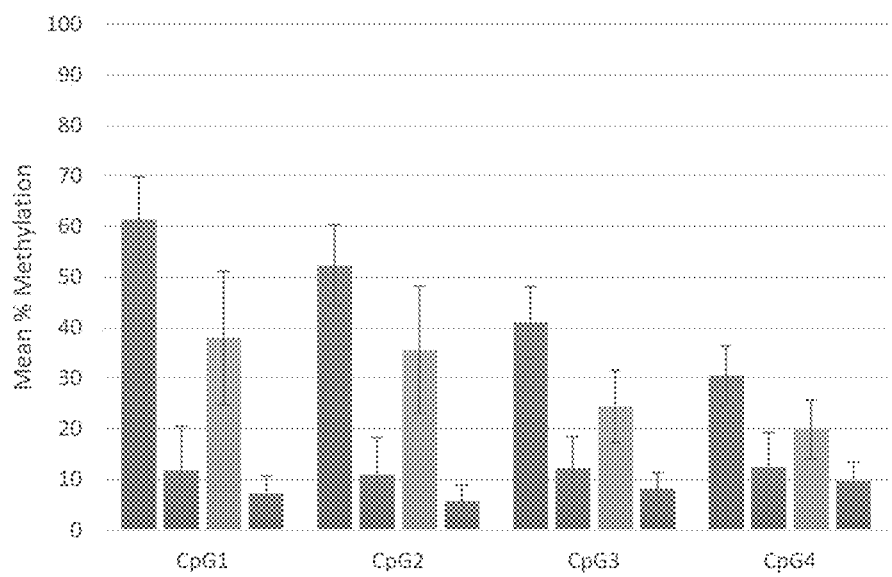
FIGS. 5A-5D provide bar graphs of the mean percent methylation of saliva (n=38), blood (n=32), vaginal epithelia (n=26) and semen (n=28) when amplified in multiplex and sequenced for the four body fluid identifying markers.
Figure 5B:
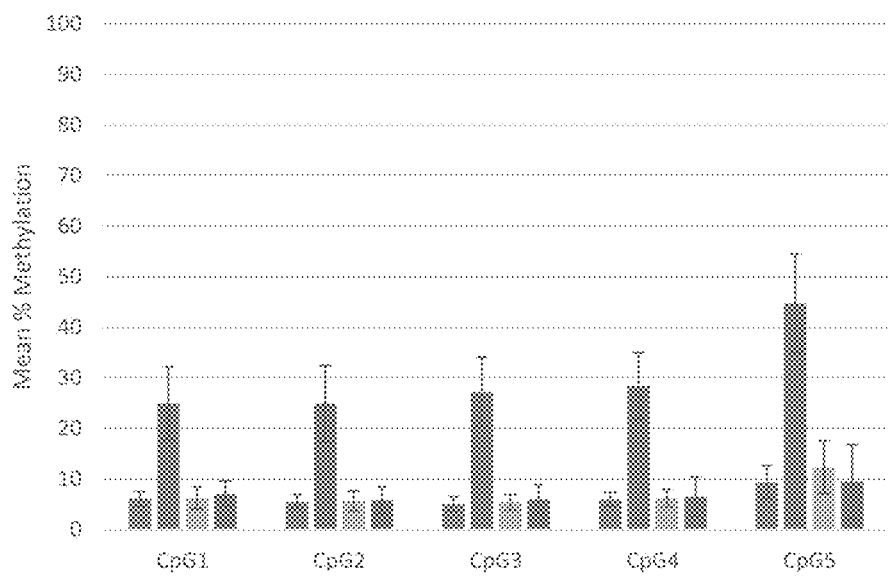
Figure 5C:
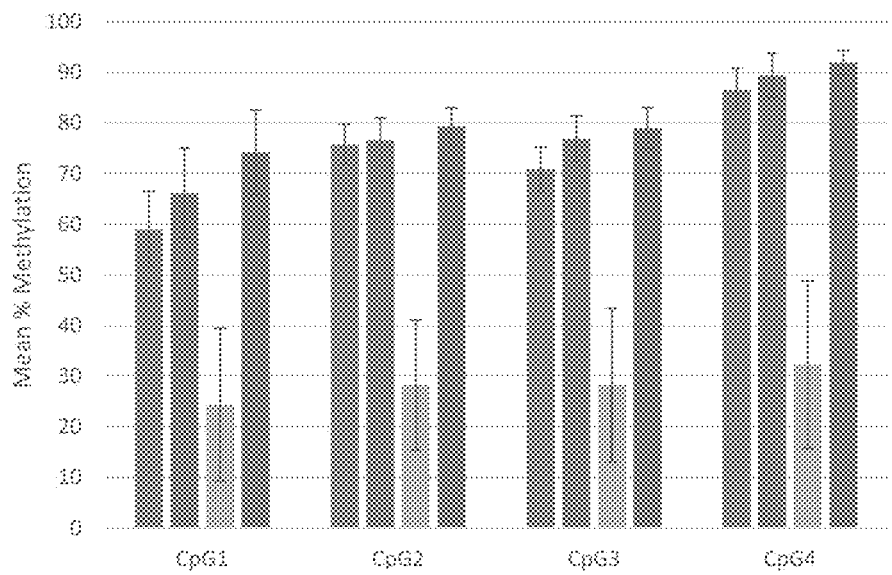
Figure 5D:
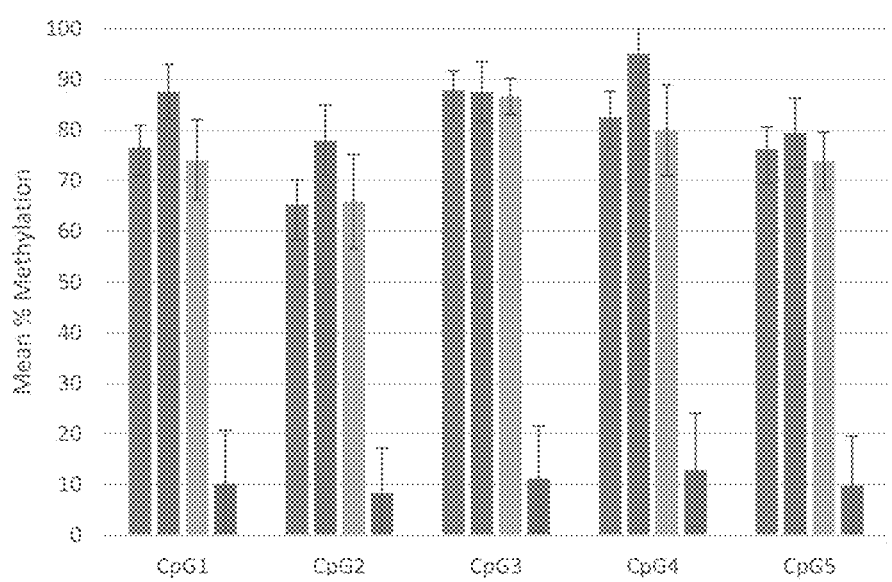
Figure 6A:
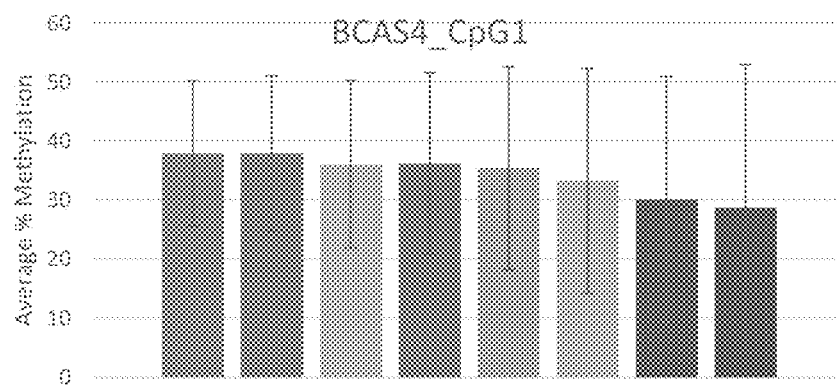
FIGS. 6A-6E provide average percent methylation for 5 vaginal samples amplified in triplicate at multiple input levels. The variation in mean percent methylation changes as the amount of DNA added to each PCR reaction decreases. Additionally, the standard deviation of recorded values at lower DNA input increases as well. Similar trends were observed in the other three body fluids. The likely cause of this loss in precision is stochastic sampling.
Figure 6B:
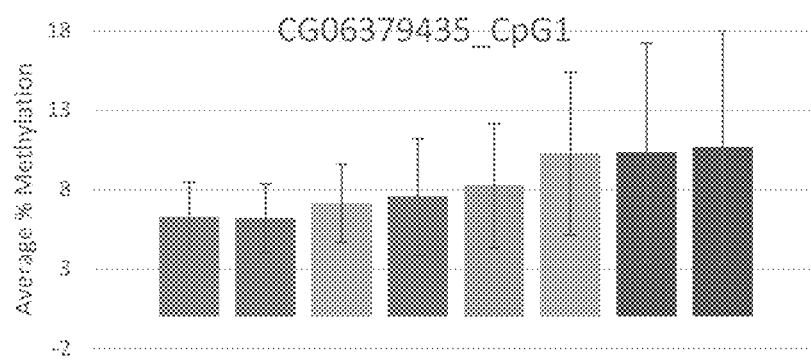
Figure 6C:
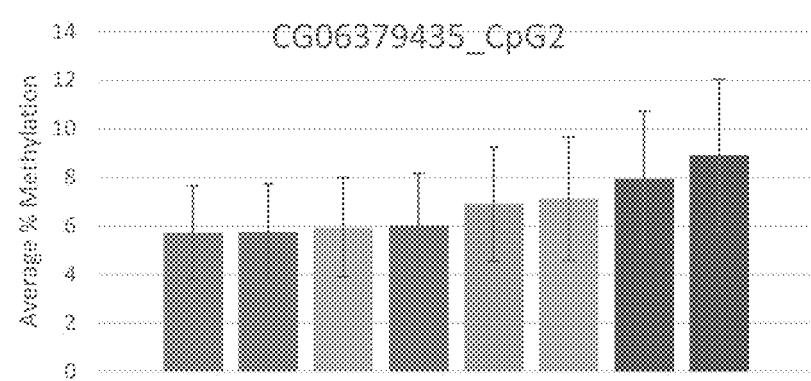
Figure 6D:
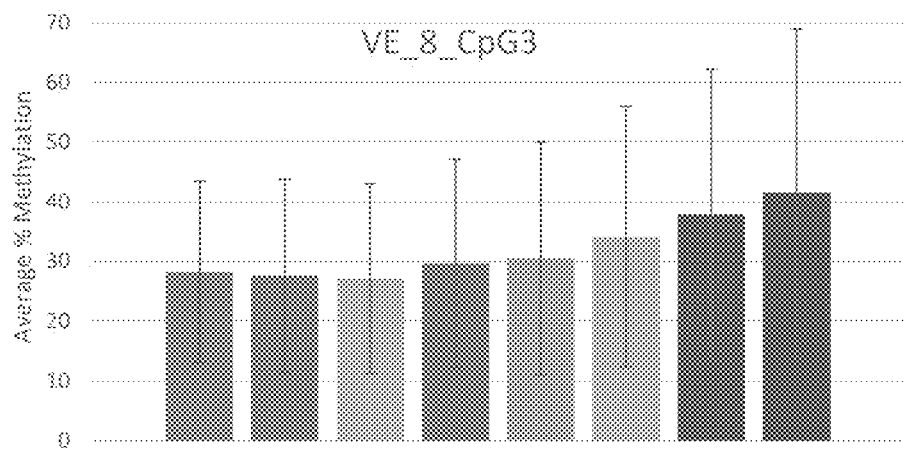
Figure 6E:
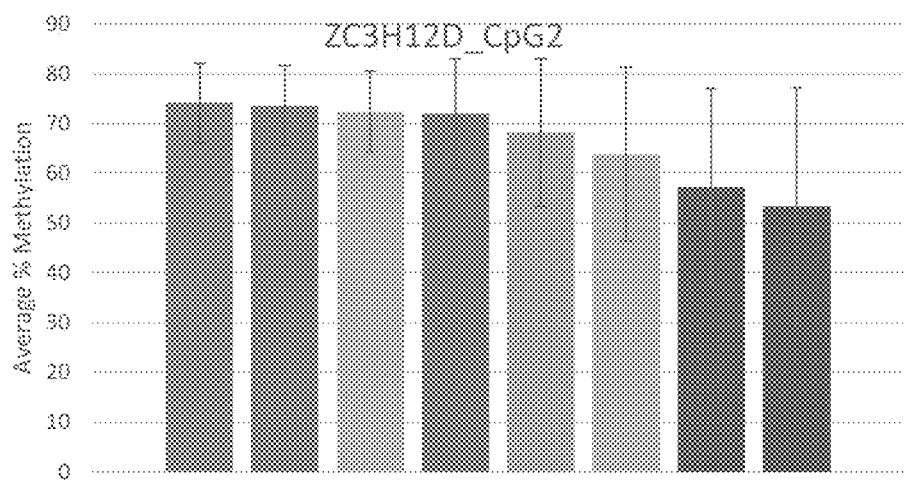

SEQ ID NO: 1: Sequence of the locus specific for vaginal epithelial cell.

SEQ ID NO: 2: Sequence of a forward primer designed to amplify the locus specific for vaginal epithelial cell.

SEQ ID NO: 3: Sequence of a reverse primer designed to amplify the locus specific for vaginal epithelial cell.

SEQ ID NO: 4: Sequence of the locus specific for vaginal epithelial cell after bisulfite treatment assuming 0% methylation of all CpG sites.

SEQ ID NO: 5: Sequence of the locus specific for vaginal epithelial cell after bisulfite treatment assuming 100% methylation of all CpG sites.

SEQ ID NO: 6: Sequence of the locus specific for sperm.

SEQ ID NO: 7: Sequence of a forward primer designed to amplify the locus specific for sperm.

SEQ ID NO: 8: Sequence of a reverse primer designed to amplify the locus specific for sperm.

SEQ ID NO: 9: Sequence of the locus specific for sperm after bisulfite treatment assuming 0% methylation of all CpG sites.

SEQ ID NO: 10: Sequence of the locus specific for sperm after bisulfite treatment assuming 100% methylation of all CpG sites.

SEQ ID NO: 11: Sequence of the locus specific for blood cells.

SEQ ID NO: 12: Sequence of a forward primer designed to amplify the locus specific for blood cells.

SEQ ID NO: 13: Sequence of a reverse primer designed to amplify the locus specific for blood cells.

SEQ ID NO: 14: Sequence of the locus specific for blood cells after bisulfite treatment assuming 0% methylation of all CpG sites.

SEQ ID NO: 15: Sequence of the locus specific for blood cells after bisulfite treatment assuming 100% methylation of all CpG sites.

SEQ ID NO: 16: Sequence of the locus specific for saliva or buccal epithelial cells.

SEQ ID NO: 17: Sequence of a forward primer designed to amplify the locus specific for buccal epithelial cells.

SEQ ID NO: 18: Sequence of a reverse primer designed to amplify the locus specific for buccal epithelial cells.

SEQ ID NO: 19: Sequence of the locus specific for buccal epithelial cells after bisulfite treatment assuming 0% methylation of all CpG sites.

SEQ ID NO: 20: Sequence of the locus specific for buccal epithelial cells after bisulfite treatment assuming 100% methylation of all CpG sites.

SEQ ID NO: 21: Sequence of the sequencing primer designed to sequence the amplicon corresponding to the locus specific for vaginal epithelial cells.

SEQ ID NO: 22: Sequence of the sequencing primer designed to sequence the amplicon corresponding to the locus specific for sperm.

SEQ ID NO: 23: Sequence of the sequencing primer designed to sequence the amplicon corresponding to the locus specific for blood cells.

SEQ ID NO: 24: Sequence of the sequencing primer designed to sequence the amplicon corresponding to the locus specific for buccal epithelial cells.

SEQ ID NO: 25: Sequence of the locus containing differentially methylated CpG positions specific for vaginal epithelial cells after bisulfite treatment assuming 0% methylation of all CpG sites.

SEQ ID NO: 26: Sequence of the locus containing differentially methylated CpG positions specific for sperms after bisulfite treatment assuming 0% methylation of all CpG sites.

SEQ ID NO: 27: Sequence of the locus containing differentially methylated CpG positions specific for blood cells after bisulfite treatment assuming 0% methylation of all CpG sites.

SEQ ID NO: 28: Sequence of the locus containing differentially methylated CpG positions specific for buccal epithelial cells after bisulfite treatment assuming 0% methylation of all CpG sites.

DETAILED DESCRIPTION OF THE INVENTION

The subject invention provides materials and methods for detecting body fluids in a sample comprising cells and/or body fluids, for example, a forensic sample, based on DNA analyses. DNA is commonly retrieved from crime scenes, and therefore, DNA isolation, storage, and general use is validated in criminal investigations. The methods described herein are time and cost-effective and require little personnel training. In one embodiment, the invention provides an assay to identify a source body fluid as semen, blood, saliva, or vaginal secretion in a sample. A further embodiment of the invention provides a multiplex assay for determining in a sample the presence of two or more body fluids and/or two or more cells selected from vaginal secretion or vaginal epithelial cell, semen or sperm, saliva or buccal epithelial cell, and blood or blood cell.

DNA methylation is one of the epigenetic mechanisms for gene regulation. Different levels of DNA methylation in certain genetic loci control gene expression by silencing or activating specific genes. The presence of a methyl group on the 5' carbon of a cytosine belonging to the dinucleotide CG (CpG) is believed to prevent the binding of the transcription machinery to the promoter of a gene. Some loci on the genome called "tissue-specific differentially methylated regions" can therefore be used for cell identification because they present different levels of DNA methylation depending on the cell studied.

In accordance with the subject invention, DNA methylation levels at specific loci are different for certain cells from body fluids when compared to other cells. For example, DNA methylation levels at specific loci are different for cells from blood, vaginal secretions, buccal epithelial cells, or sperm. Accordingly, in certain embodiments of the invention, methylation status at specific genetic loci in the genomic DNA is determined and used to identify the source of body fluid in a sample.

The nucleotide coordinates for genetic loci mentioned herein correspond to University of California Santa Cruz genome browser and Assembly hg19.

Identifying vaginal epithelial cells based on DNA methylation methods provided herein is performed by determining DNA methylation at a vaginal epithelial cell specific locus. In one embodiment, determining DNA methylation at the vaginal epithelial cell specific locus is performed through the use of a specific primer pair that amplifies the vaginal epithelial cell specific locus, having the sequence of SEQ ID NO: 1, from bisulfite-treated genomic DNA. For example, an amplicon corresponding to the vaginal epithelial cell specific locus can be obtained by PCR using bisulfite-treated genomic DNA as template and a primer pair having the sequences of SEQ ID NOs: 2 and 3.

The vaginal epithelial cell specific locus having the sequence of SEQ ID NO: 1 is also referred to as VE_8 in this disclosure. The vaginal epithelial cell specific locus, VE_8, is a locus of 131 base pairs on chromosome 16 and occupies the chromosomal location from 86398381 to 86398511. As such, the genome coordinates for VE_8 are chr16: 86398381-86398511. VE_8 contains CpG sites that are hypomethylated in the genomes of vaginal epithelial cells compared to other cells, particularly, buccal epithelial cells, blood cells, or sperm. Particularly, cytosine residues located at positions 39, 75, 87, and 97 are hypomethylated in the genomes of vaginal epithelial cells compared to other cells, particularly, buccal epithelial cells, blood cells, or sperm.

A portion of SEQ ID NO: 1 containing the differentially methylated CpG positions is provided in SEQ ID NO: 25. Based on the CpG positions in SEQ ID NO: 1 as provided in the previous paragraph, a person of ordinary skill in the art can identify the corresponding CpG positions in SEQ ID NO: 25. Also, a person of ordinary skill in the art can design primer pairs designed to amplify SEQ ID NO: 25 based on the sequence of SEQ ID NO: 4 that spans the sequence of SEQ ID NO: 25. In preferred embodiments, each primer of such primer pairs has a sequence complementary to a portion of the sequence of SEQ ID NO: 4 that spans the sequence of SEQ ID NO: 25 and has between 15 and 30 nucleotides.

Identifying sperm based on DNA methylation methods provided herein is performed by determining DNA methylation at a sperm specific locus. In one embodiment, determining DNA methylation at the sperm specific locus is performed through the use of a specific primer pair that amplifies a sperm specific locus, having the sequence of SEQ ID NO: 6, from the bisulfite-treated genomic DNA. An amplicon corresponding to the sperm specific locus is obtained by PCR using bisulfite-treated genomic DNA as template and a primer pair having the sequences of SEQ ID NOs: 7 and 8.

The sperm specific locus having the sequence of SEQ ID NO: 6 is also referred to as ZC3H12D in this disclosure. The sperm specific locus, ZC3H12D, is a locus of 91 base pairs on chromosome 6 and occupies the chromosomal location from 149778061 to 149778151. As such, the genome coordinates for ZC3H12D are chr6: 149778061-149778151. ZC3H12D contains CpG sites that are hypomethylated in the genomes of sperm cells compared to other cells, particularly, buccal epithelial cells, blood cells, or vaginal epithelial cells. Particularly, cytosine residues located at positions 43, 45, 55, 62, and 67 are hypomethylated in the genomes of sperm cells compared to other cells, particularly, buccal epithelial cells, blood cells, or vaginal epithelial cells.

A portion of SEQ ID NO: 6 containing the differentially methylated CpG positions is provided in SEQ ID NO: 26. Based on the CpG positions in SEQ ID NO: 6 as provided in the previous paragraph, a person of ordinary skill in the art can identify the corresponding CpG positions in SEQ ID NO: 26. Also, a person of ordinary skill in the art can design primer pairs designed to amplify SEQ ID NO: 26 based on the sequence of SEQ ID NO: 9 that spans the sequence of SEQ ID NO: 26. In preferred embodiments, each primer of such primer pairs has a sequence complementary to a portion of the sequence of SEQ ID NO: 9 that spans the sequence of SEQ ID NO: 26 and has between 15 and 30 nucleotides.

Identifying blood cells based on DNA methylation methods provided herein is performed by determining DNA methylation at a blood cell specific locus. In one embodiment, determining DNA methylation at the blood cell specific locus is performed through the use of a specific primer pair that amplifies a blood cell specific locus, having the sequence of SEQ ID NO: 11, from the bisulfite-treated genomic DNA. An amplicon corresponding to the blood cell specific locus is obtained by PCR using bisulfate-treated genomic DNA as template and a primer pair having the sequences of SEQ ID NOs: 12 and 13.

The blood cell specific locus having the sequence of SEQ ID NO: 11 is also referred to as CG06379435 in this disclosure. The blood cell specific locus, CG06379435, is a locus of 210 base pairs on chromosome 19 and occupies the chromosomal location from 3344114 to 3344322. As such, the genome coordinates for CG06379435 are chr19: 3344114-3344322. CG06379435 contains CpG sites that are hypermethylated in the genome of blood cells compared to other cells, particularly, buccal epithelial cells, vaginal epithelial cells, or sperm. Particularly, cytosine residues located at positions 129, 138, 153, 160, and 167 are hypermethylated in the genome of blood cells compared to other cells, particularly, buccal epithelial cells, vaginal epithelial cells, or sperm.

A portion of SEQ ID NO: 11 containing the differentially methylated CpG positions is provided in SEQ ID NO: 27. Based on the CpG positions in SEQ ID NO: 11 as provided in the previous paragraph, a person of ordinary skill in the art can identify the corresponding CpG positions in SEQ ID NO: 27. Also, a person of ordinary skill in the art can design primer pairs designed to amplify SEQ ID NO: 27 based on the sequence of SEQ ID NO: 14 that spans the sequence of SEQ ID NO: 27. In preferred embodiments, each primer of such primer pairs has a sequence complementary to a portion of the sequence of SEQ ID NO: 14 that spans the sequence of SEQ ID NO: 27 and has between 15 and 30 nucleotides.

Identifying buccal epithelial cells based on DNA methylation methods provided herein is performed by determining DNA methylation at a buccal epithelial cell specific locus. In one embodiment, determining DNA methylation at the buccal epithelial cell specific locus is performed through the use of a specific primer pair that amplifies a buccal epithelial cell specific locus, having the sequence of SEQ ID NO: 16, from the bisulfite-treated genomic DNA. An amplicon corresponding to the buccal epithelial cell specific locus is obtained by PCR using bisulfate-treated genomic DNA as template and a primer pair having the sequences of SEQ ID NOs: 17 and 18.

The buccal epithelial cell specific locus having the sequence of SEQ ID NO: 16 is also referred to as BCAS4 in this disclosure. The buccal epithelial cell specific locus, BCAS4, is a locus of 158 base pairs on chromosome 20 and occupies the chromosomal location from 49410802 to 49410959. As such, the genome coordinates for BCAS4 are chr20: 49410802-49410959. BCAS4 contains CpG sites that are hypermethylated in the genome of buccal epithelial cells compared to other cells, particularly, blood cells, vaginal epithelial cells, or sperm. Particularly, cytosine residues located at positions 64, 69, 81, and 88 are hypermethylated in the genome of buccal epithelial cells compared to other cells, particularly, blood cells, vaginal epithelial cells, or sperm.

A portion of SEQ ID NO: 16 containing the differentially methylated CpG positions is provided in SEQ ID NO: 28. Based on the CpG positions in SEQ ID NO: 16 as provided in the previous paragraph, a person of ordinary skill in the art can identify the corresponding CpG positions in SEQ ID NO: 28. Also, a person of ordinary skill in the art can design primer pairs designed to amplify SEQ ID NO: 28 based on the sequence of SEQ ID NO: 19 that spans the sequence of SEQ ID NO: 28. In preferred embodiments, each primer of such primer pairs has a sequence complementary to a portion of the sequence of SEQ ID NO: 19 that spans the sequence of SEQ ID NO: 28 and has between 15 and 30 nucleotides.

The methods described herein can be practiced with minute amounts of genomic DNA, for example, between 1 ng to 50 ng, particularly, between 5 ng to 30 ng, more particularly, at about 20 ng. Moreover, methylation levels at specific loci described herein, for example, SEQ ID NOs: 1, 6, 11, and 16, can be performed when mixtures of body fluids are present.

Accordingly, one embodiment of the invention provides a method for identifying a sample as containing, or not containing, one or more cells selected from a vaginal epithelial cell, a sperm, a blood cell, or a buccal epithelial cell, the method comprising the steps of:
  a) determining the level of methylation at the genetic loci corresponding to one or more of SEQ ID NOs: 1, 6, 11, and 16, in:
    i) a genomic DNA isolated from the sample, and
    ii) optionally, a control genomic DNA;
  b) optionally, obtaining one or more reference values corresponding to the levels of methylation at the genetic loci corresponding to one or more of SEQ ID NOs: 1, 6, 11, and 16; and
  c) identifying the sample as:
    i) containing or not containing the vaginal epithelial cell based on the level of methylation at the genetic locus corresponding to SEQ ID NO: 1 in the genomic DNA isolated from the sample,
    ii) containing or not containing the sperm based on the level of methylation at the genetic locus corresponding to SEQ ID NO: 6 in the genomic DNA isolated from the sample,
    iii) containing or not containing the blood cell based on the level of methylation at the genetic locus corresponding to SEQ ID NO: 11 in the genomic DNA isolated from the sample, and/or
    iv) containing or not containing the buccal epithelial cell based on the level of methylation at the genetic locus corresponding to SEQ ID NO: 16 in the genomic DNA isolated from the sample.

In certain embodiments, the invention provides a method for identifying a sample as containing, or not containing, one or more cells selected from a vaginal epithelial cell, a sperm, a blood cell, or a buccal epithelial cell, the method comprising the steps of:
  a) determining the level of methylation at the genetic loci corresponding to one or more of SEQ ID NOs: 25, 26, 27, and 28, in:
    i) a genomic DNA isolated from the sample, and
    ii) optionally, a control genomic DNA;
  b) optionally, obtaining one or more reference values corresponding to the levels of methylation at the genetic loci corresponding to one or more of SEQ ID NOs: 25, 26, 27, and 28; and
  c) identifying the sample as:
    i) containing or not containing the vaginal epithelial cell based on the level of methylation at the genetic locus corresponding to SEQ ID NO: 25 in the genomic DNA isolated from the sample,
    ii) containing or not containing the sperm based on the level of methylation at the genetic locus corresponding to SEQ ID NO: 26 in the genomic DNA isolated from the sample,
    iii) containing or not containing the blood cell based on the level of methylation at the genetic locus corresponding to SEQ ID NO: 27 in the genomic DNA isolated from the sample, and/or
    iv) containing or not containing the buccal epithelial cell based on the level of methylation at the genetic locus corresponding to SEQ ID NO: 28 in the genomic DNA isolated from the sample.

In certain embodiments, the methods described herein to identify a sample as containing a vaginal epithelial cell, sperm, blood cell, or a buccal epithelial cell are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, or buccal epithelial cell before the step of isolating the genomic DNA. In an even further embodiment, the methods are practiced on a forensic sample that is known to contain only vaginal epithelial cells, sperms, blood cells, or buccal epithelial cells or a combination thereof.

In one embodiment, the invention provides a method for identifying a sample as containing, or not containing, a vaginal epithelial cell, the method comprising the steps of:
  a) determining the level of methylation at the genetic locus corresponding to SEQ ID NO: 1 in:
    i) a genomic DNA isolated from the sample, and
    ii) optionally, a control genomic DNA;
  b) optionally, obtaining one or more reference values corresponding to the level of methylation at the genetic locus corresponding to SEQ ID NO: 1; and
  c) identifying the sample as:
    i) containing or not containing the vaginal epithelial cell based on the level of methylation at the genetic locus corresponding to SEQ ID NO: 1 in the genomic DNA isolated from the sample.

In certain such embodiments, the methods further comprise identifying a sample as containing, or not containing, one or more cells selected from a sperm, a blood cell, and a buccal epithelial cell, the method comprising the steps of:

a) determining the level of methylation at the genetic loci corresponding to one or more of SEQ ID NOs: 6, 11, and 16, in:
   i) a genomic DNA isolated from the sample, and
   ii) optionally, a control genomic DNA;
b) optionally, obtaining one or more reference values corresponding to the levels of methylation at the genetic loci corresponding to one or more of SEQ ID NOs: 6, 11, and 16; and
c) identifying the sample as:
   i) containing or not containing the sperm based on the level of methylation at the genetic locus corresponding to SEQ ID NO: 6 in the genomic DNA isolated from the sample,
   ii) containing or not containing the blood cell based on the level of methylation at the genetic locus corresponding to SEQ ID NO: 11 in the genomic DNA isolated from the sample, and/or
   iii) containing or not containing the buccal epithelial cell based on the level of methylation at the genetic locus corresponding to SEQ ID NO: 16 in the genomic DNA isolated from the sample.

In another embodiment, the invention provides a method for identifying a sample as containing, or not containing, a sperm, the method comprising the steps of:
a) determining the level of methylation at the genetic locus corresponding to SEQ ID NO: 6 in:
   i) a genomic DNA isolated from the sample, and
   ii) optionally, a control genomic DNA;
b) optionally, obtaining one or more reference values corresponding to the level of methylation at the genetic locus corresponding to SEQ ID NO: 6; and
c) identifying the sample as:
   i) containing or not containing the vaginal epithelial cell based on the level of methylation at the genetic locus corresponding to SEQ ID NO: 6 in the genomic DNA isolated from the sample.

In certain such embodiments, the methods further comprise identifying a sample as containing, or not containing, one or more cells selected from a vaginal epithelial cell, a blood cell, and a buccal epithelial cell, the method comprising the steps of:
a) determining the level of methylation at the genetic loci corresponding to one or more of SEQ ID NOs: 1, 11, and 16, in:
   i) a genomic DNA isolated from the sample, and
   ii) optionally, a control genomic DNA;
b) optionally, obtaining one or more reference values corresponding to the levels of methylation at the genetic loci corresponding to one or more of SEQ ID NOs: 1, 11, and 16; and
c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the blood cell based on the level of methylation at the genetic locus corresponding to SEQ ID NO: 11 in the genomic DNA isolated from the sample, and/or
   iii) containing or not containing the buccal epithelial cell based on the level of methylation at the genetic locus corresponding to SEQ ID NO: 16 in the genomic DNA isolated from the sample.

In a further embodiment, the invention provides a method for identifying a sample as containing, or not containing, a blood cell, the method comprising the steps of:
a) determining the level of methylation at the genetic locus corresponding to SEQ ID NO: 11 in:
   i) a genomic DNA isolated from the sample, and
   ii) optionally, a control genomic DNA;
b) optionally, obtaining one or more reference values corresponding to the level of methylation at the genetic locus corresponding to SEQ ID NO: 11; and
c) identifying the sample as:
   i) containing or not containing the vaginal epithelial cell based on the level of methylation at the genetic locus corresponding to SEQ ID NO: 11 in the genomic DNA isolated from the sample.

In certain such embodiments, the methods further comprise identifying a sample as containing, or not containing, one or more cells selected from a vaginal epithelial cell, a sperm, and a buccal epithelial cell, the method comprising the steps of:
a) determining the level of methylation at the genetic loci corresponding to one or more of SEQ ID NOs: 1, 6, and 16, in:
   i) a genomic DNA isolated from the sample, and
   ii) optionally, a control genomic DNA;
b) optionally, obtaining one or more reference values corresponding to the levels of methylation at the genetic loci corresponding to one or more of SEQ ID NOs: 1, 6, and 16; and
c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the sperm based on the level of methylation at the genetic locus corresponding to SEQ ID NO: 6 in the genomic DNA isolated from the sample, and/or
   iii) containing or not containing the buccal epithelial cell based on the level of methylation at the genetic locus corresponding to SEQ ID NO: 16 in the genomic DNA isolated from the sample.

In an even further embodiment, the invention provides a method for identifying a sample as containing, or not containing, a buccal epithelial cell, the method comprising the steps of:
a) determining the level of methylation at the genetic locus corresponding to SEQ ID NO: 16 in:
   i) a genomic DNA isolated from the sample, and
   ii) optionally, a control genomic DNA;
b) optionally, obtaining one or more reference values corresponding to the level of methylation at the genetic locus corresponding to SEQ ID NO: 16; and
c) identifying the sample as:
   i) containing or not containing the buccal epithelial cell based on the level of methylation at the genetic locus corresponding to SEQ ID NO: 16 in the genomic DNA isolated from the sample.

In certain such embodiments, the methods further comprise identifying a sample as containing, or not containing, one or more cells selected from a vaginal epithelial cell, a sperm, and a blood cell, the method comprising the steps of:
a) determining the level of methylation at the genetic loci corresponding to one or more of SEQ ID NOs: 1, 6, and 11, in:
   i) a genomic DNA isolated from the sample, and
   ii) optionally, a control genomic DNA;

b) optionally, obtaining one or more reference values corresponding to the levels of methylation at the genetic loci corresponding to one or more of SEQ ID NOs: 1, 6, and 11; and c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the sperm based on the level of methylation at the genetic locus corresponding to SEQ ID NO: 6 in the genomic DNA isolated from the sample, and/or
   iii) containing or not containing the blood cell based on the level of methylation at the genetic locus corresponding to SEQ ID NO: 11 in the genomic DNA isolated from the sample.

Similar to the multiplex embodiments described above, determining the methylation levels at the genetic loci corresponding to one or more of SEQ ID NOs: 25, 26, 27, and/or 28 can also be performed in a singleplex or multiplex format.

In certain embodiments, the methods described herein to identify a sample as containing a vaginal epithelial cell, sperm, blood cell, a buccal epithelial cell, or a combination thereof are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, buccal epithelial cell, or a combination thereof before the step of isolating the genomic DNA. In an even further embodiment, the methods are practiced on a forensic sample that is known to contain only vaginal epithelial cells, sperms, blood cells, buccal epithelial cells, or a combination thereof. The control sample used in the methods of the invention can be obtained from one or more of the following: a known vaginal epithelial cell, a known sperm, a known blood cell, and a known buccal epithelial cell. The control sample can also be a cell other than a vaginal epithelial cell, sperm, blood cell, or buccal epithelial cell and that is known to have methylation levels at the specific genetic loci corresponding to SEQ ID NOs: 1, 6, 11, and 16 to be different from the methylation levels at SEQ ID NOs: 1, 6, 11, and 16 from a vaginal epithelial cell, sperm, blood cell, and buccal epithelial cell, respectively.

If the control sample is a vaginal epithelial cell, the step of identifying the sample as containing the vaginal epithelial cell is based on the level of methylation at the genetic locus corresponding to SEQ ID NO: 1 in the genomic DNA isolated from the sample being similar to the level of methylation at the genetic locus corresponding to SEQ ID NO: 1 in the control genomic DNA. Also, if the control sample is a vaginal epithelial cell, the step of identifying the sample as not containing the vaginal epithelial cell is based on the level of methylation at the genetic locus corresponding to SEQ ID NO: 1 in the genomic DNA isolated from the sample being different from the level of methylation at the genetic locus corresponding to SEQ ID NO: 1 in the control genomic DNA.

If the control sample is a cell different from a vaginal epithelial cell, the step of identifying the sample as containing the vaginal epithelial cell is based on the level of methylation at the genetic locus corresponding to SEQ ID NO: 1 in the genomic DNA isolated from the sample being different from the level of methylation at the genetic locus corresponding to SEQ ID NO: 1 in the control genomic DNA. Also, if the control sample is a cell different from a vaginal epithelial cell, the step of identifying the sample as not containing the vaginal epithelial cell is based on the level of methylation at the genetic locus corresponding to SEQ ID NO: 1 in the genomic DNA isolated from the sample being similar to the level of methylation at the genetic locus corresponding to SEQ ID NO: 1 in the control genomic DNA.

The reference value corresponding to the level of methylation at the genetic locus corresponding to SEQ ID NO: 1 can indicate the level of methylation at the genetic locus corresponding to SEQ ID NO: 1 in a vaginal epithelial cell or a cell other than a vaginal epithelial cell. As such, the reference value corresponding to level of methylation at the genetic locus corresponding to SEQ ID NO: 1 can indicate the presence or absence of a vaginal epithelial cell. In a vaginal epithelial cell, the genetic locus VE_8 is methylated at less than about 30%, less than about 25%, less than about 20%, less than about 15%, less than about 10%, less than about 5%, or less than about 1%.

Similarly, if the control sample is a sperm, the step of identifying the sample as containing the sperm is based on the level of methylation at the genetic locus corresponding to SEQ ID NO: 6 in the genomic DNA isolated from the sample being similar to the level of methylation at the genetic locus corresponding to SEQ ID NO: 6 in the control genomic DNA. Also, if the control sample is a sperm, the step of identifying the sample as not containing the sperm is based on the level of methylation at the genetic locus corresponding to SEQ ID NO: 6 in the genomic DNA isolated from the sample being different from the level of methylation at the genetic locus corresponding to SEQ ID NO: 6 in the control genomic DNA.

If the control sample is a cell different from a sperm, the step of identifying the sample as containing the sperm is based on the level of methylation at the genetic locus corresponding to SEQ ID NO: 6 in the genomic DNA isolated from the sample being different from the level of methylation at the genetic locus corresponding to SEQ ID NO: 6 in the control genomic DNA. Also, if the control sample is a cell different from a sperm, the step of identifying the sample as not containing the sperm is based on the level of methylation at the genetic locus corresponding to SEQ ID NO: 6 in the genomic DNA isolated from the sample being similar to the level of methylation at the genetic locus corresponding to SEQ ID NO: 6 in the control genomic DNA.

The reference value corresponding to the level of methylation at the genetic locus corresponding to SEQ ID NO: 6 can indicate the level of methylation at the genetic locus corresponding to SEQ ID NO: 6 in a sperm or a cell other than a sperm. As such, the reference value corresponding to level of methylation at the genetic locus corresponding to SEQ ID NO: 6 can indicate the presence or absence of a sperm. In a sperm, the genetic locus ZC3H12D is methylated at less than about 20%, less than about 15%, less than about 10%, less than about 5%, or less than about 1%.

Further, if the control sample is a blood cell, the step of identifying the sample as containing the blood cell is based on the level of methylation at the genetic locus corresponding to SEQ ID NO: 11 in the genomic DNA isolated from the sample being similar to the level of methylation at the genetic locus corresponding to SEQ ID NO: 11 in the control genomic DNA. Also, if the control sample is a blood cell, the step of identifying the sample as not containing the blood cell is based on the level of methylation at the genetic locus corresponding to SEQ ID NO: 11 in the genomic DNA isolated from the sample being different from the level of methylation at the genetic locus corresponding to SEQ ID NO: 11 in the control genomic DNA.

If the control sample is a cell different from a blood cell, the step of identifying the sample as containing the blood cell is based on the level of methylation at the genetic locus corresponding to SEQ ID NO: 11 in the genomic DNA isolated from the sample being different from the level of methylation at the genetic locus corresponding to SEQ ID NO: 11 in the control genomic DNA. Also, if the control sample is a cell different from a blood cell, the step of identifying the sample as not containing the blood cell is based on the level of methylation at the genetic locus corresponding to SEQ ID NO: 11 in the genomic DNA isolated from the sample being similar to the level of methylation at the genetic locus corresponding to SEQ ID NO: 11 in the control genomic DNA.

The reference value corresponding to the level of methylation at the genetic locus corresponding to SEQ ID NO: 11 can indicate the level of methylation at the genetic locus corresponding to SEQ ID NO: 11 in a blood cell or a cell other than a blood cell. As such, the reference value corresponding to level of methylation at the genetic locus corresponding to SEQ ID NO: 11 can indicate the presence or absence of a blood cell. In a blood cell, the genetic locus CG06379435 is methylated at more than about 20%, more than about 25%, more than about 30%, more than about 35%, or more than about 40%.

Furthermore, if the control sample is a buccal epithelial cell, the step of identifying the sample as containing the buccal epithelial cell is based on the level of methylation at the genetic locus corresponding to SEQ ID NO: 16 in the genomic DNA isolated from the sample being similar to the level of methylation at the genetic locus corresponding to SEQ ID NO: 16 in the control genomic DNA. Also, if the control sample is a buccal epithelial cell, the step of identifying the sample as not containing the buccal epithelial cell is based on the level of methylation at the genetic locus corresponding to SEQ ID NO: 16 in the genomic DNA isolated from the sample being different from the level of methylation at the genetic locus corresponding to SEQ ID NO: 16 in the control genomic DNA.

If the control sample is a cell different from a buccal epithelial cell, the step of identifying the sample as containing the buccal epithelial cell is based on the level of methylation at the genetic locus corresponding to SEQ ID NO: 16 in the genomic DNA isolated from the sample being different from the level of methylation at the genetic locus corresponding to SEQ ID NO: 16 in the control genomic DNA. Also, if the control sample is a cell different from a buccal epithelial cell, the step of identifying the sample as not containing the buccal epithelial cell is based on the level of methylation at the genetic locus corresponding to SEQ ID NO: 16 in the genomic DNA isolated from the sample being similar to the level of methylation at the genetic locus corresponding to SEQ ID NO: 16 in the control genomic DNA.

The reference value corresponding to the level of methylation at the genetic locus corresponding to SEQ ID NO: 16 can indicate the level of methylation at the genetic locus corresponding to SEQ ID NO: 16 in a buccal epithelial cell or a cell other than a buccal epithelial cell. As such, the reference value corresponding to level of methylation at the genetic locus corresponding to SEQ ID NO: 16 can indicate the presence or absence of a buccal epithelial cell. In a buccal epithelial cell, the genetic locus BCAS4 is methylated at more than about 30%, more than about 35%, more than about 40%, more than about 45%, more than about 50%, or more than about 60%.

In certain embodiments, a buccal epithelial cell cannot be distinguished from a vaginal epithelial cell simply based on the methylation status at the genetic locus corresponding to SEQ ID NO: 16. In such embodiments, a buccal epithelial cell is distinguished from a vaginal epithelial cell based on the methylation status of the VE_8 marker, which is specific for vaginal epithelial cells.

In one embodiment, the level of methylation of specific genetic loci are used to determine the purity of a preparation of a cell comprising or consisting of one or more of a vaginal epithelial cell, sperm, blood cell, and buccal epithelial cell.

For example, if a vaginal epithelial cell sample is obtained, the level of methylation at the VE_8 locus can be checked in the sample to identify the purity of the vaginal epithelial cells in the sample. For example, if the VE_8 genetic locus is less than about 20% methylated, the vaginal epithelial cell sample is almost 100% pure; whereas, if the VE_8 genetic locus is about 50% methylated, the vaginal epithelial cell sample is not pure and may contain other types cells, particularly, sperms, blood cells, or buccal epithelial cells.

Similarly, if a sperm sample is obtained, the level of methylation at the ZC3H12D locus can be checked in the sample to identify the purity of the sperm sample. For example, if the ZC3H12D genetic locus is less than about 10% methylated, the sperm sample is almost 100% pure; whereas, if the ZC3H12D genetic locus is about 50% methylated, the sperm sample is not pure and may contain other types cells, particularly, vaginal epithelial cells, blood cells, or buccal epithelial cells.

Further, if a blood cell sample is obtained, the level of methylation at the CG06379435 locus can be checked in the sample to identify the purity of the blood cell sample. For example, if the CG06379435 genetic locus is more than about 20% methylated, the blood cell sample is almost 100% pure; whereas, if the CG06379435 genetic locus is less than about 20% methylated, the blood cell sample is not pure and may contain other types cells, particularly, vaginal epithelial cells, sperms, or buccal epithelial cells.

Furthermore, if a buccal epithelial cell sample is obtained, the level of methylation at the BCAS4 locus can be checked in the sample to identify the purity of the buccal epithelial cell sample. For example, if the BCAS4 genetic locus is more than about 30% methylated, the buccal epithelial cell sample is almost 100% pure; whereas, if the BCAS4 genetic locus is less than about 30% methylated, the buccal epithelial cell sample is not pure and may contain other types cells, particularly, vaginal epithelial cells, sperms, or blood cells.

Various techniques are known to a person of ordinary skill in the art to determine the level of methylation at the specific loci in a genomic DNA. Non-limiting examples of such techniques include bisulfite conversion, HRM, digestion by restriction enzymes followed by PCR, Combined Bisulfite Restriction Analysis (COBRA), direct sequencing, cloning and sequencing, bisulfite treatment and sequences, bisulfite treatment and pyrosequencing, mass spectrometry analysis or probe/microarray based assay. Certain techniques of determining methylation at certain genomic sites are described in Eads et al., Xiong et al., Paul et al., Warnecke et al., Tost et al., and Ehrich et al., the contents of which are herein incorporated in their entirety. Additional techniques for determining the level of methylation at a genetic are known to a person of ordinary skill in the art and such techniques are within the purview of the invention.

In a particular embodiment, the levels of methylation at the specific loci in a genomic DNA obtained from a sample are determined by sequencing the genetic locus after bisulfite treatment. Bisulfite treatment of genomic DNA chemically changes the unmethylated cytosines to uracil, while the methylated cytosines are unchanged. In the PCR reaction using primers designed to amplify a specific locus, uracils are copied as thymines making the PCR product produced from an un-methylated locus to contain thymines in place of cytosines compared to the PCR product produced from a methylated locus, which contains cytosines. As such, methylation of the specific locus can be determined based on the sequence of the amplicon, i.e., higher content of cytosines indicates a methylated locus and higher content of thymines indicates an un-methylated locus.

Determining the levels of methylation at the specific loci in a genomic DNA obtained from a sample by sequencing comprises the steps of: obtaining the sample, isolating genomic DNA from the sample, treating the isolated DNA with bisulfite, PCR amplifying the genetic loci using specifically designed primers to produce amplicons corresponding to the genetic loci, determining the sequence of the amplicons produced in the PCR using a sequencing primer, and determining the levels of methylation at the specific loci in a genomic DNA based on the sequence of the amplicons. The methylation status at the specific genetic loci can be used to identify the source of body fluid based.

In one embodiment, a primer pair designed to amplify the genetic locus corresponding to SEQ ID NO: 1 comprises a forward primer comprising SEQ ID NO: 2 and a reverse primer comprising SEQ ID NO: 3. A skilled artisan can design primer pairs other than SEQ ID NOs: 2 and 3 to amplify the genetic locus VE_8 based on the sequence of SEQ ID NO: 1 and the sequences of the regions flanking VE_8 in the genomic DNA. Such embodiments are within the purview of the invention. In certain embodiments, the amplicon produced by amplifying the genetic locus corresponding to SEQ ID NO: 1 is sequenced using a sequencing primer comprising SEQ ID NO: 21. A skilled artisan can design sequencing primers other than SEQ ID NO: 21 to sequence the amplicon corresponding to the genetic locus VE_8 based on the sequence of SEQ ID NO: 1 and the sequences of the regions flanking VE_8 in the genomic DNA and such embodiments are within the purview of the invention.

In another embodiment, a primer pair designed to amplify the genetic locus corresponding to SEQ ID NO: 6 comprises a forward primer comprising SEQ ID NO: 7 and a reverse primer comprising SEQ ID NO: 8. A skilled artisan can design primer pairs other than SEQ ID NOs: 7 and 8 to amplify the genetic locus ZC3H12D based on the sequence of SEQ ID NO: 6 and the sequences of the regions flanking ZC3H12D in the genomic DNA. Such embodiments are within the purview of the invention. In certain embodiments, the amplicon produced by amplifying the genetic locus corresponding to SEQ ID NO: 6 is sequenced using a sequencing primer comprising SEQ ID NO: 22. A skilled artisan can design sequencing primers other than SEQ ID NO: 22 to sequence the amplicon corresponding to the genetic locus ZC3H12D based on the sequence of SEQ ID NO: 6 and the sequences of the regions flanking ZC3H12D in the genomic DNA and such embodiments are within the purview of the invention.

In a further embodiment, a primer pair designed to amplify the genetic locus corresponding to SEQ ID NOs: 11 comprises a forward primer comprising SEQ ID NO: 12 and a reverse primer comprising SEQ ID NO: 13. A skilled artisan can design primer pairs other than SEQ ID NOs: 12 and 13 to amplify the genetic locus CG06379435 based on the sequences of SEQ ID NOs: 11 and the sequences of regions flanking CG06379435 in the genomic DNA. Such embodiments are within the purview of the invention. In certain embodiments, the amplicon produced by amplifying the genetic locus corresponding to SEQ ID NO: 11 is sequenced using a sequencing primer comprising SEQ ID NO: 23. A skilled artisan can design sequencing primers other than SEQ ID NO: 23 to sequence the amplicon corresponding to the genetic locus CG06379435 based on the sequence of SEQ ID NO: 11 and the sequences of the regions flanking CG06379435 in the genomic DNA and such embodiments are within the purview of the invention.

In an even further embodiment, a primer pair designed to amplify the genetic locus corresponding to SEQ ID NOs: 16 comprises a forward primer comprising SEQ ID NO: 17 and a reverse primer comprising SEQ ID NO: 18. A skilled artisan can design primer pairs other than SEQ ID NOs: 17 and 18 to amplify the genetic locus BCAS4 based on the sequence of SEQ ID NOs: 16 and the sequences of the regions flanking BCAS4 in the genomic DNA. Such embodiments are within the purview of the invention. In certain embodiments, the amplicon produced by amplifying the genetic locus corresponding to SEQ ID NO: 16 is sequenced using a sequencing primer comprising SEQ ID NO: 24. A skilled artisan can design sequencing primers other than SEQ ID NO: 24 to sequence the amplicon corresponding to the genetic locus BCAS4 based on the sequence of SEQ ID NO: 16 and the sequences of the regions flanking BCAS4 in the genomic DNA and such embodiments are within the purview of the invention.

Accordingly, in one embodiment, the invention provides a method for identifying a sample as containing, or not containing, one or more cells selected from a vaginal epithelial cell, a sperm, a blood cell, or a buccal epithelial cell, the method comprising the steps of:

a) isolating genomic DNA from the sample and optionally, a control sample;
  b) treating the isolated genomic DNA with bisulfate;
  c) PCR amplifying the genetic loci corresponding to one or more of SEQ ID NOs: 1, 6, 11, and 16 to produce the corresponding one or more amplicons, wherein the PCR amplifying is performed using one or more primer pairs selected from:
    i) SEQ ID NOs: 2 and 3,
    ii) SEQ ID NOs: 7 and 8.
    iii) SEQ ID NOs: 12 and 13, or
    iv) SEQ ID NOs: 17 and 18; and
  d) determining the sequences of the amplicons corresponding to one or more of SEQ ID NOs: 1, 6, 11, and 16; and
  e) identifying the sample as:
  i) containing or not containing the vaginal epithelial cell based on the sequence of the amplicon corresponding to the genetic locus corresponding to SEQ ID NO: 1 in the genomic DNA isolated from the sample,
  ii) containing or not containing the sperm based on the sequence of the amplicon corresponding to the genetic locus corresponding to SEQ ID NO: 6 in the genomic DNA isolated from the sample,
  iii) containing or not containing the blood cell based on the sequence of the amplicon corresponding to the genetic locus corresponding to SEQ ID NO: 11 in the genomic DNA isolated from the sample, and/or
  iv) containing or not containing the buccal epithelial cell based on the sequence of the amplicon corresponding to the genetic locus corresponding to SEQ ID NO: 16 in the genomic DNA isolated from the sample.

In one embodiment the sequence of the amplicon corresponding to the genetic loci corresponding to SEQ ID NOs: 1, 6, 11, or 16 are identified using a sequencing primer comprising SEQ ID NOs: 21, 22, 23, or 24, respectively. A skilled artisan can design additional sequencing primers to sequence the amplicons corresponding to the genetic loci corresponding to SEQ ID NOs: 1, 6, 11, or 16 based on the sequences of these genetic loci and the sequences of the regions flanking these genetic loci in the genomic DNA. Such embodiments are within the purview of the invention.

In another embodiment, a sequencing primer can be designed based on an adapter introduced into the amplicon by incorporating the adapter into one of the forward or reverse primers. An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the adapter can be used to sequence the amplicon.

In a specific embodiment, the invention provides a method for identifying a sample as containing, or not containing a vaginal epithelial cell based on the methylation level of SEQ ID NO: 1 determined using the amplification primer pair of SEQ ID NO: 2 and 3 and a sequencing primer of SEQ ID NO: 21. Such methods can further comprise identifying a sample as containing, or not containing, one or more cells selected from a sperm, a blood cell, and a buccal epithelial cell, based on the methylation level of one or more of SEQ ID NOs: 6, 11, and 16 determined using the primer pairs of SEQ ID NOs: 7 and 8, 12 and 13, and 17 and 18, respectively, and sequencing primers of SEQ ID NOs: 22, 23, and 24, respectively.

In another embodiment, the invention provides a method for identifying a sample as containing, or not containing a sperm based on the methylation level of SEQ ID NO: 6 determined using the primer pair of SEQ ID NO: 7 and 8 and a sequencing primer of SEQ ID NO: 22. Such methods can further comprise identifying a sample as containing, or not containing, one or more cells selected from a vaginal epithelial cell, a blood cell, and a buccal epithelial cell, based on the methylation level of one or more of SEQ ID NOs: 1, 11, and 16 determined using the primer pairs of SEQ ID NOs: 2 and 3, 12 and 13, and 17 and 18, respectively, and sequencing primers of SEQ ID NOs: 21, 23, and 24, respectively.

In a further embodiment, the invention provides a method for identifying a sample as containing, or not containing a blood cell based on the methylation level of SEQ ID NO: 11 determined using the primer pair of SEQ ID NO: 12 and 13 and a sequencing primer of SEQ ID NO: 23. Such methods can further comprise identifying a sample as containing, or not containing, one or more cells selected from a vaginal epithelial cell, a sperm, and a buccal epithelial cell, based on the methylation level of one or more of SEQ ID NOs: 1, 6, and 16 determined using the primer pairs of SEQ ID NOs: 2 and 3, 7 and 8, and 17 and 18, respectively, and sequencing primers of SEQ ID NOs: 21, 22, and 24, respectively.

In an even further embodiment, the invention provides a method for identifying a sample as containing, or not containing a buccal epithelial cell based on the methylation level of SEQ ID NO: 16 determined using the primer pair of SEQ ID NO: 17 and 18 and a sequencing primer of SEQ ID NO: 24. Such methods can further comprise identifying a sample as containing, or not containing, one or more cells selected from a vaginal epithelial cell, a sperm, and a blood cell based on the methylation level of one or more of SEQ ID NOs: 1, 6, and 11 determined using the primer pairs of SEQ ID NOs: 2 and 3, 7 and 8, and 12 and 13, respectively, and sequencing primers of SEQ ID NOs: 21, 22, and 23, respectively.

In certain embodiments, the methods described herein to identify a sample as containing a vaginal epithelial cell, sperm, blood cell, or a buccal epithelial cell are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, or buccal epithelial cell before the step of isolating the genomic DNA.

In one embodiment, the sequences of one or more amplicons corresponding to the genetic loci corresponding to SEQ ID NOs: 1, 6, 11, and 16 are compared to the genomic sequence to determine the methylation status of the genetic loci corresponding to SEQ ID NOs: 1, 6, 11, and 16, which in turn is used to identify the sample as containing or not containing one or more cells selected from a vaginal epithelial cell, a sperm, a blood cell, or a buccal epithelial cell.

The four primer sets described above would amplify genomic DNA isolated from samples containing one or more of vaginal epithelial cells or vaginal secretions, sperms or semen, blood or blood cells, and buccal epithelial cell or saliva. The identification of different body fluids is made only after amplification and further analysis, for example, sequencing analysis.

The primer pairs amplify bisulfite treated genomic DNA regardless of its methylation status and would not amplify genomic DNA that is not bisulfite treated. Therefore, if the DNA sample is not appropriate for PCR amplification, for example, due to a low amount of DNA or presence of impurities, the amplicons will not be produced.

A control DNA sample added can be used and treated in the same manner as a test sample to ensure that the reagents are working properly. Therefore, if a test sample fails to produce amplicons, the sample can be identified as a source of a problem for lack of amplification despite having working reagents. Likewise a negative control can be run where water replaces the genomic DNA to ensure that any amplification is not due to unspecific amplification arising from contaminated reagents.

A control primer pair can also be used that would amplify genomic DNA that is not bisulfite converted. The presence of an amplicon for this primer pair would tell a user that the bisulfite conversion was not successful. Therefore, instead of having an amplification that did not work for an unknown reason, a user would identify a failed bisulfite conversion.

In certain embodiments, a control genomic DNA can comprise DNA that is not bisulfite treated. Therefore, each locus has a "control primer set" directed to a bisulfite untreated genomic DNA sequence and a "test primer sequence" directed to bisulfite treated genomic DNA. Therefore, for every test, one can have a multiplex primer set directed to a bisulfite treated test genomic DNA and a multiplex primer set directed to a bisulfite untreated control genomic DNA.

One embodiment of the invention provides a method for determining the levels of methylation at genetic loci corresponding to one or more of SEQ ID NOs: 1, 6, 11, and 16, in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, 11, and 16, and
(d) analyzing the PCR amplicons produced in step c) to determine the level of methylation at the genetic loci corresponding to one or more of SEQ ID NOs: 1, 6, 11, and 16.

In a specific embodiment, the invention provides a method for determining the levels of methylation at the genetic locus corresponding to SEQ ID NO: 1 in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 1, and
(d) analyzing the PCR amplicons produced in step c) to determine the level of methylation at the genetic locus corresponding to SEQ ID NO: 1.

Certain such embodiments further comprise determining the levels of methylation at genetic loci corresponding to one or more of SEQ ID NOs: 6, 11, and 16, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 6, 11, and 16, and
(d) analyzing the PCR amplicons produced in step c) to determine the level of methylation at the genetic loci corresponding to one or more of SEQ ID NOs: 6, 11, and 16.

In another embodiment, the invention provides a method for determining the levels of methylation at the genetic locus corresponding to SEQ ID NO: 6 in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 6, and
(d) analyzing the PCR amplicons produced in step c) to determine the level of methylation at the genetic locus corresponding to SEQ ID NO: 6.

Certain such embodiments further comprise determining the levels of methylation at genetic loci corresponding to one or more of SEQ ID NOs: 1, 11, and 16, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 11, and 16, and
(d) analyzing the PCR amplicons produced in step c) to determine the level of methylation at the genetic loci corresponding to one or more of SEQ ID NOs: 1, 11, and 16.

In a further embodiment, the invention provides a method for determining the levels of methylation at the genetic locus corresponding to SEQ ID NO: 11 in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 11, and
(d) analyzing the PCR amplicons produced in step c) to determine the level of methylation at the genetic locus corresponding to SEQ ID NO: 11.

Certain such embodiments further comprise determining the levels of methylation at genetic loci corresponding to one or more of SEQ ID NOs: 1, 6, and 16, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, and 16, and
(d) analyzing the PCR amplicons produced in step c) to determine the level of methylation at the genetic loci corresponding to one or more of SEQ ID NOs: 1, 6, and 16.

In an even further embodiment, the invention provides a method for determining the levels of methylation at the genetic locus corresponding to SEQ ID NO: 16 in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 16, and
(d) analyzing the PCR amplicons produced in step c) to determine the level of methylation at the genetic locus corresponding to SEQ ID NO: 16.

Certain such embodiments further comprise determining the levels of methylation at genetic loci corresponding to one or more of SEQ ID NOs: 1, 6, and 11, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, and 11, and
(d) analyzing the PCR amplicons produced in step c) to determine the level of methylation at the genetic loci corresponding to one or more of SEQ ID NOs: 1, 6, and 11.

The details described above regarding the techniques for determining the level of methylation at the genetic loci corresponding to one or more SEQ ID NOs: 1, 6, 11, or 16 in the genomic DNA in a sample based on the analysis of the amplicons produced in the PCR amplification steps are also applicable to the method for determining the levels of methylation at these genetic loci. The primer pairs designed to amplify these genetic loci, sequencing primers and other details described above are also applicable to the method for determining the levels of methylation at these genetic loci.

In one embodiment of a multiplex reaction, genomic DNA is isolated from a sample and a PCR is conducted in the presence of two, three, or four primer pairs designed to amplify the genetic loci corresponding to one or more of SEQ ID NOs: 1, 6, 11, and 16. For example, genomic DNA is isolated from a sample and a PCR is conducted in the presence of two, three, or four primer pairs selected from SEQ ID NOs: 2 and 3, SEQ ID NOs: 7 and 8, SEQ ID NOs: 12, and 13, and SEQ ID NOs: 17 and 18. After amplification, each of two, three, or four aliquots of the reaction mixture is sequenced using a sequencing primer selected from SEQ ID NOs: 21, 22, 23, and 24. Based on the sequences identified using the sequencing primers, the presence of two or more cells selected from vaginal epithelial cells, sperm, blood cells, or buccal epithelial cells is determined.

A further embodiment of the invention provides a kit comprising one or more primer pairs designed to amplify the genetic loci corresponding to one or more SEQ ID NOs: 1, 6, 11, or 16 in a bisulfate treated human genomic DNA. In one embodiment, the kit comprises one or more primer pairs selected from:
 i) a primer pair having the sequences of SEQ ID NOs: 2 and 3,
 ii) a primer pair having the sequences of SEQ ID NOs: 7 and 8,
 iii) a primer pair having the sequences of SEQ ID NOs: 12 and 13, and
 iv) a primer pair having the sequences of SEQ ID NOs: 17 and 18.

A skilled artisan can design additional primer pairs to amplify the genetic loci corresponding to one or more SEQ ID NOs: 1, 6, 11, or 16 based on the sequences of these genetic loci and the sequences of flanking regions in the genomic DNA and such embodiments are within the purview of the invention.

In addition to the primer pairs, the kit may further comprise a sequencing primer designed to sequence the amplicon produced from the primer pairs. Accordingly, the kit comprises one or more primer pairs and sequencing primers selected from:
 i) a primer pair having the sequences of SEQ ID NOs: 2 and 3 and a sequencing primer comprising SEQ ID NO: 21,
 ii) a primer pair having the sequences of SEQ ID NOs: 7 and 8 and a sequencing primer comprising SEQ ID NO: 22,
 iii) a primer pair having the sequences of SEQ ID NOs: 12 and 13 and a sequencing primer comprising SEQ ID NO: 23, and
 iv) a primer pair having the sequences of SEQ ID NOs: 17 and 18 and a sequencing primer comprising SEQ ID NO: 24.

In one embodiment, the invention provides a kit comprising a primer pair of SEQ ID NOs: 2 and 3, optionally, further comprising, one or more primer pairs selected from:
 i) a primer pair having the sequences of SEQ ID NOs: 7 and 8,
 ii) a primer pair having the sequences of SEQ ID NOs: 12 and 13, and
 iii) a primer pair having the sequences of SEQ ID NOs: 17 and 18.

In another embodiment, the invention provides a kit comprising a primer pair of SEQ ID NOs: 7 and 8, optionally, further comprising, one or more primer pairs selected from:
 i) a primer pair having the sequences of SEQ ID NOs: 2 and 3,
 ii) a primer pair having the sequences of SEQ ID NOs: 12 and 13, and
 iii) a primer pair having the sequences of SEQ ID NOs: 17 and 18.

In a further embodiment, the invention provides a kit comprising a primer pair of SEQ ID NOs: 12 and 13, optionally, further comprising, one or more primer pairs selected from:
 i) a primer pair having the sequences of SEQ ID NOs: 2 and 3,
 ii) a primer pair having the sequences of SEQ ID NOs: 7 and 8, and
 iii) a primer pair having the sequences of SEQ ID NOs: 17 and 18.

In an even further embodiment, the invention provides a kit comprising a primer pair of SEQ ID NOs: 17 and 18, optionally, further comprising, one or more primer pairs selected from:
 i) a primer pair having the sequences of SEQ ID NOs: 2 and 6,
 ii) a primer pair having the sequences of SEQ ID NOs: 7 and 8, and
 iii) a primer pair having the sequences of SEQ ID NOs: 12 and 13.

In one embodiment, the invention provides a kit comprising a primer pair of SEQ ID NOs: 2 and 3 and a sequencing primer comprising SEQ ID NO: 21, optionally, further comprising, one or more primer pairs and sequencing primers selected from:
 i) a primer pair having the sequences of SEQ ID NOs: 7 and 8 and a sequencing primer comprising SEQ ID NO: 22,
 ii) a primer pair having the sequences of SEQ ID NOs: 12 and 13 and a sequencing primer comprising SEQ ID NO: 23, and
 iii) a primer pair having the sequences of SEQ ID NOs: 17 and 18 and a sequencing primer comprising SEQ ID NO: 24.

In another embodiment, the invention provides a kit comprising a primer pair of SEQ ID NOs: 7 and 8 and a sequencing primer comprising SEQ ID NO: 22, optionally, further comprising, one or more primer pairs and sequencing primers selected from:
 i) a primer pair having the sequences of SEQ ID NOs: 2 and 3 and a sequencing primer comprising SEQ ID NO: 21,
 ii) a primer pair having the sequences of SEQ ID NOs: 12 and 13 and a sequencing primer comprising SEQ ID NO: 23, and
 iii) a primer pair having the sequences of SEQ ID NOs: 17 and 18 and a sequencing primer comprising SEQ ID NO: 24.

In a further embodiment, the invention provides a kit comprising a primer pair of SEQ ID NOs: 12 and 13 and a sequencing primer comprising SEQ ID NO: 23, optionally, further comprising, one or more primer pairs and sequencing primers selected from:
 i) a primer pair having the sequences of SEQ ID NOs: 2 and 3 and a sequencing primer comprising SEQ ID NO: 21,
 ii) a primer pair having the sequences of SEQ ID NOs: 7 and 8 and a sequencing primer comprising SEQ ID NO: 22, and
 iii) a primer pair having the sequences of SEQ ID NOs: 17 and 18 and a sequencing primer comprising SEQ ID NO: 24.

In an even further embodiment, the invention provides a kit comprising a primer pair of SEQ ID NOs: 17 and 18 and a sequencing primer comprising SEQ ID NO: 24, optionally, further comprising, one or more primer pairs and sequencing primers selected from:
  i) a primer pair having the sequences of SEQ ID NOs: 2 and 3 and a sequencing primer comprising SEQ ID NO: 21,
  ii) a primer pair having the sequences of SEQ ID NOs: 7 and 8 and a sequencing primer comprising SEQ ID NO: 22, and
  iii) a primer pair having the sequences of SEQ ID NOs: 12 and 13 and a sequencing primer comprising SEQ ID NO: 23.

Certain embodiments of the invention also provide a kit comprising one or more primer pairs, and optionally, one or more sequencing primers, selected from:
  i) a primer pair designed to amplify the sequence of SEQ ID NO: 25 and optionally, a sequencing primer designed to sequence the amplified sequence, wherein each primer of the primer pair and when present, the sequencing primer, has a sequence complementary to a portion of the sequence of SEQ ID NO: 4 that spans the sequence of SEQ ID NO: 25 and has between 15 and 30 nucleotides,
  ii) a primer pair designed to amplify the sequence of SEQ ID NO: 26, and optionally, a sequencing primer designed to sequence the amplified sequence wherein each primer of the primer pair and when present, the sequencing primer, has a sequence complementary to a portion of the sequence of SEQ ID NO: 9 that spans the sequence of SEQ ID NO: 26 and has between 15 and 30 nucleotides,
  iii) a primer pair designed to amplify the sequence of SEQ ID NO: 27, and optionally, a sequencing primer designed to sequence the amplified sequence, wherein each primer of the primer pair, and when present, the sequencing primer, has a sequence complementary to a portion of the sequence of SEQ ID NO: 14 that spans the sequence of SEQ ID NO: 27 and has between 15 and 30 nucleotides, and
  iv) a primer pair designed to amplify the sequence of SEQ ID NO: 28, and optionally, a sequencing primer designed to sequence the amplified sequence, wherein each primer of the primer pair and when present, the sequencing primer, has a sequence complementary to a portion of the sequence of SEQ ID NO: 19 that spans the sequence of SEQ ID NO: 28 and has between 15 and 30 nucleotides.

In preferred embodiments, such kits comprise:
  i) the primer pair designed to amplify the sequence of SEQ ID NO: 25 and the sequencing primer designed to sequence the amplified sequence,
  ii) the primer pair designed to amplify the sequence of SEQ ID NO: 26 and the sequencing primer designed to sequence the amplified sequence,
  iii) the primer pair designed to amplify the sequence of SEQ ID NO: 27 and the sequencing primer designed to sequence the amplified sequence, and/or
  iv) the primer pair designed to amplify the sequence of SEQ ID NO: 28 and the sequencing primer designed to sequence the amplified sequence.

In further embodiments, the kit comprises one or more reagents, for example, reagents for treating a sample, reagents for isolating cells from the sample, reagents for isolating genomic DNA from the sample, reagents for bisulfite treating the genomic DNA, reagents for conducting PCR, and reagents for conducting pyrosequencing.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%). In the context of melting temperatures where the term "about" is used, the melting temperatures are within 0.45° C. of the stated melting temperature.

As used herein, the term "level of methylation" or "methylation status" as applied to a genetic locus refers to whether one or more cytosine residues present in a CpG have or do not have a methyl group. The level of methylation or methylation status refers to the percentage of cells in a sample that do or do not have a methyl group on such cytosines. For example, if 50 cells in a pool of 100 cells contain methylated cytosines at a CpG site, the level of methylation or methylation status of the CpG site is 50%.

A primer pair is a pair of oligonucleotides, each having about 15 to 30 nucleotides, and designed to amplify a specific locus from template DNA. Guidelines for designing a primer pair to amplify a specific locus to in a template DNA are well known in the art.

A singleplex PCR is a reaction where only one set of primers is used per reaction; whereas, a multiplex reaction is one that uses multiple primer sets per PCR reaction.

As used herein the phrase "the genetic loci corresponding to a sequence identifier in a bisulfite treated genomic DNA" indicates the region of the bisulfite treated genomic DNA comprising the recited sequence. Accordingly, the phrase "an amplicon corresponding to a genetic locus corresponding to a sequence identifier" indicates an amplicon produced by PCR amplification of a bisulfite treated genomic DNA comprising the recited sequence. However, because of the bisulfite treatment of the genomic DNA, the amplicon corresponding to a genetic locus corresponding to a sequence identifier may not have a sequence identical to the sequence of the genetic locus. Particularly, methylated cytosine residues in the genetic locus would be present as thymine residues in the amplicons corresponding to the genetic locus and guanine residues based paired with methylated cytosine residues in the genetic locus would be present as adenine residues in the amplicons corresponding to the genetic locus.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Designing Primers for Genomic Loci Specific for a Body Fluid

DNA from known body fluids can be used in single reactions, i.e., in a singleplex. Initially primer pairs in singleplex PCR reactions are tested. The primers are designed herein to amplify a specific locus in the genomic DNA regardless of methylation status of the genomic locus. Because amplification is independent of methylation, for body fluid identification the primers are designed to amplify a region that presents a different methylation status for the target body fluid when compared to the other body fluids, allowing distinction by sequencing and methylation status analysis (FIGS. 1 to 4).

Multiplex analysis is performed with two, three, or four primer pairs. The primer pairs can be selected from:
i) a primer pair (VE_8) designed to amplify a specific locus in the genomic DNA from vaginal epithelial cells,
ii) a primer pair (CG06379435) designed to amplify a specific locus in the genomic DNA from blood,
iii) a primer pair (ZC3H12D) designed to amplify a specific locus in the genomic DNA from sperm,
iv) a primer pair (BCAS4) designed to amplify a specific locus in the genomic DNA from buccal epithelial cell.

After the amplification reaction, each of one, two, three, or four aliquots of the PCR reaction mixture is sequenced using a primer selected from SEQ ID NOs: 21, 22, 23, or 24.

Example 2—DNA Methylation Analysis for Body Fluid Identification

Several DNA methylation markers were located and validated for identifying a source of DNA as blood, saliva, vaginal epithelia, or semen. The loci BCAS4, CG06379435, VE_8, and ZC3H12D show hypomethylation in certain body fluids and hypermethylation in other body fluids. These four loci were analyzed in a multiplex PCR assay to demonstrate their ability to accurately identify the source of DNA as one of the four body fluids.

A population study, sensitivity study, degradation study, and inhibition study were performed. The population study included the data of 120 samples. For sensitivity study, the multiplex was tested with input DNA from 20 ng to 100 pg. For degradation study, the samples were exposed to 95° C. for 10-25 minutes, and for inhibition study, samples were exposed to hematin and humic acid at concentrations of 0.08 mM and 0.24 mg/mL, respectively.

The population study allowed for a cluster analysis to correctly group all samples by body fluid. The sensitivity study showed the method working reliably with low levels of input, however, for certain loci there were increased deviations from the mean percent methylation at sub ng input levels. In the degradation study, no adverse effects were observed until samples had been heated at 95° C. for 20 minutes. Hematin and humic acid did not significantly affect the results when added to the sample before bisulfite conversion.

Population Study: Approximately 30 samples each of saliva, blood, vaginal epithelia, and semen were sequenced using the body fluid multiplex. Results were analyzed via cluster analysis, ANOVA and Tukey Test (FIGS. 5A-6D, Tables 1-2).

Sensitivity Study: Multiplex was amplified with input DNA of 20 ng, 10 ng, 5 ng, 2 ng, 1 ng, 500 pg, 250 pg, and 100 pg (FIGS. 6A-6E).

Figure 7A:
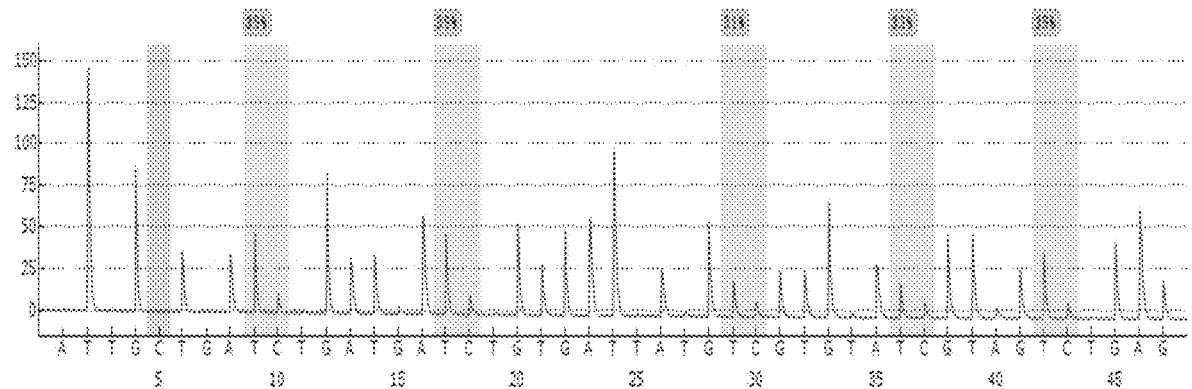
FIG. 7A-7C provide data for DNA samples with (A) no humic acid added, (B) 0.24 mg/mL of humic acid before bisulfite conversion and (C) 0.24 mg/mL of humic acid added after bisulfite conversion. The process of bisulfite conversion acts as a secondary wash step for the DNA sample, as demonstrated by the fact that the resulting amplified DNA is only slightly inhibited, whereas the DNA sample that received humic acid after bisulfite conversion failed to amplify.
Figure 7B:
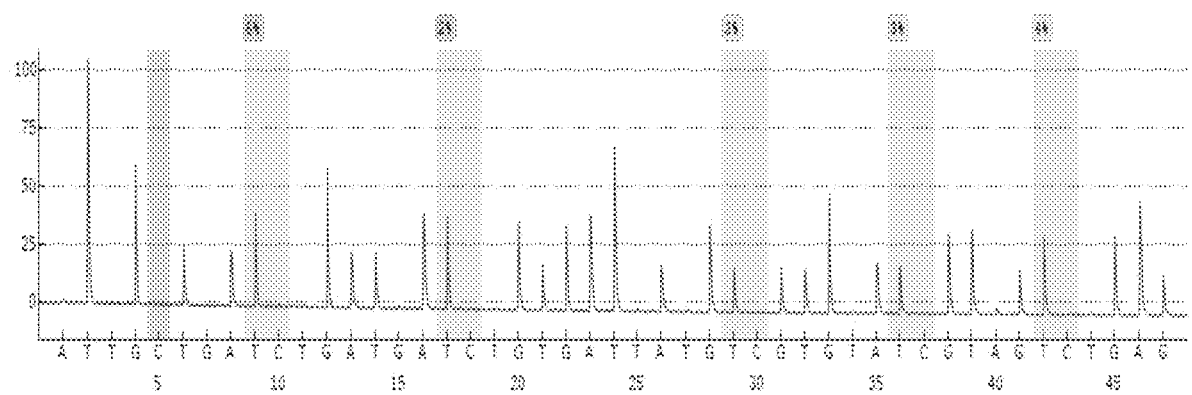
Figure 7C:
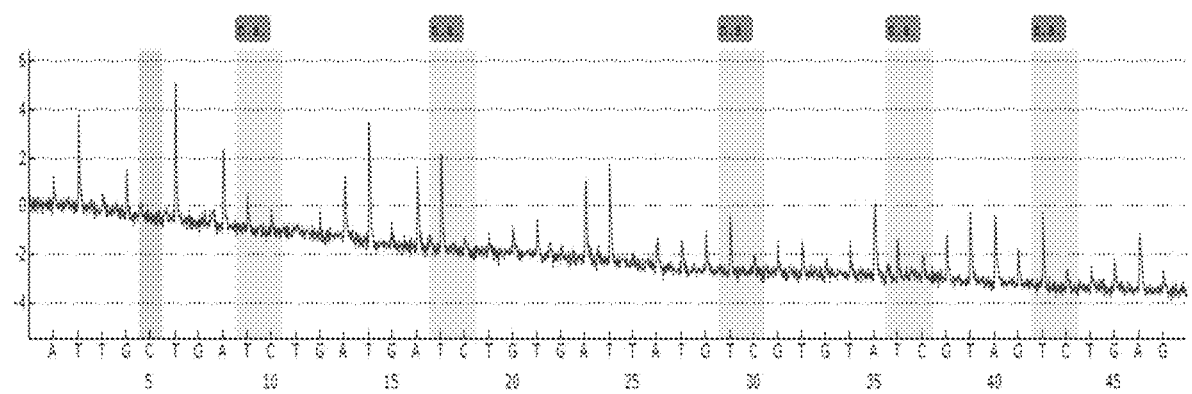
Figure 8A:
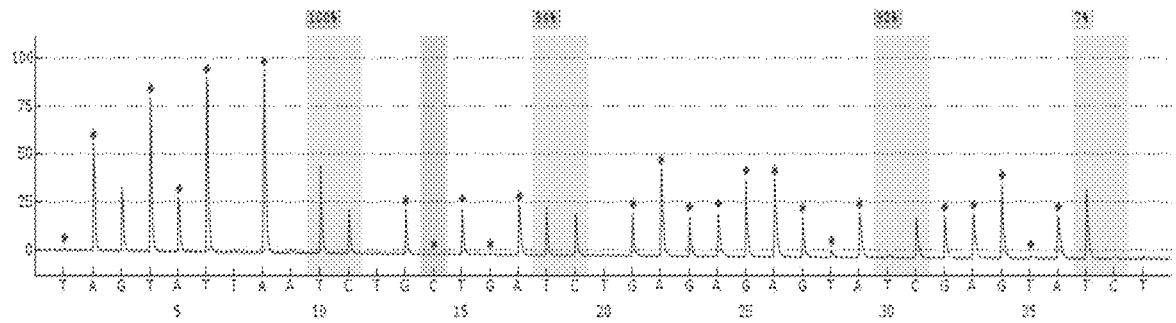
FIGS. 8A-8D provide data for DNA samples incubated at room temperature for 20 minutes (A), 95° C. for 14 minutes (B), 95° C. for 20 minutes (C), and 95° C. for 25 minutes (D). The increased time at higher temperatures resulted in a higher level of degradation in the DNA samples. This then caused a less efficient amplification of the DNA and reduced peak heights in the final pyrograms.
Figure 8B:
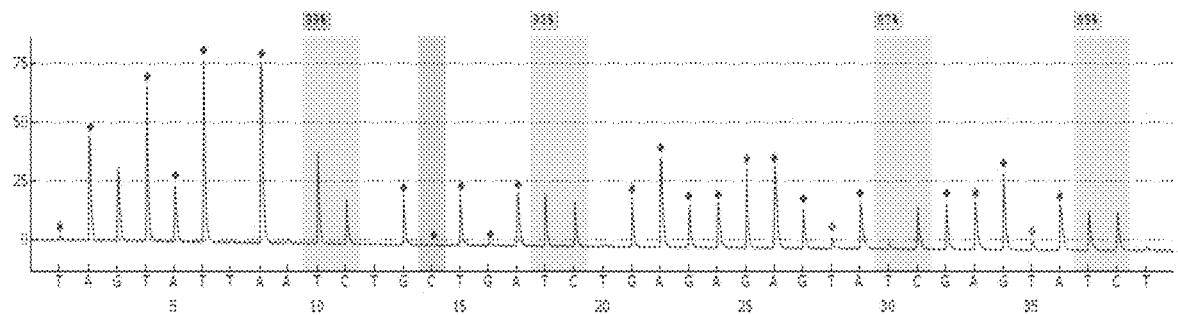
Figure 8C:
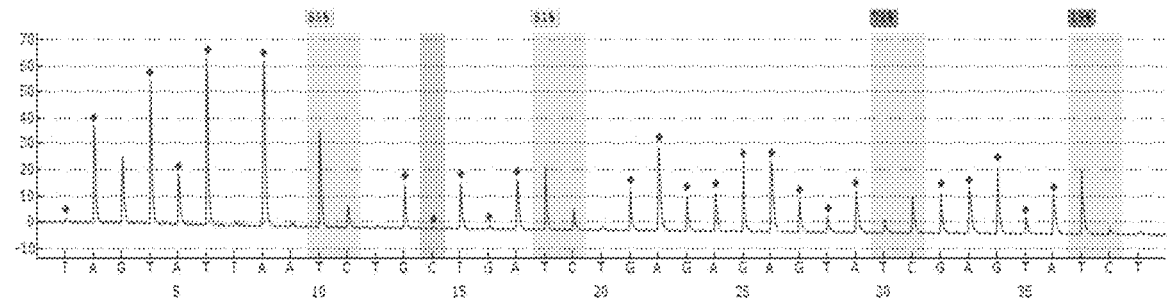
Figure 8D:
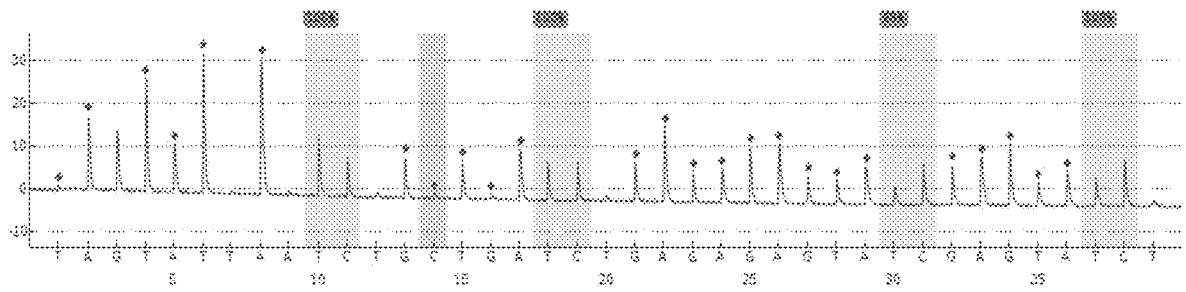
Figure 9:
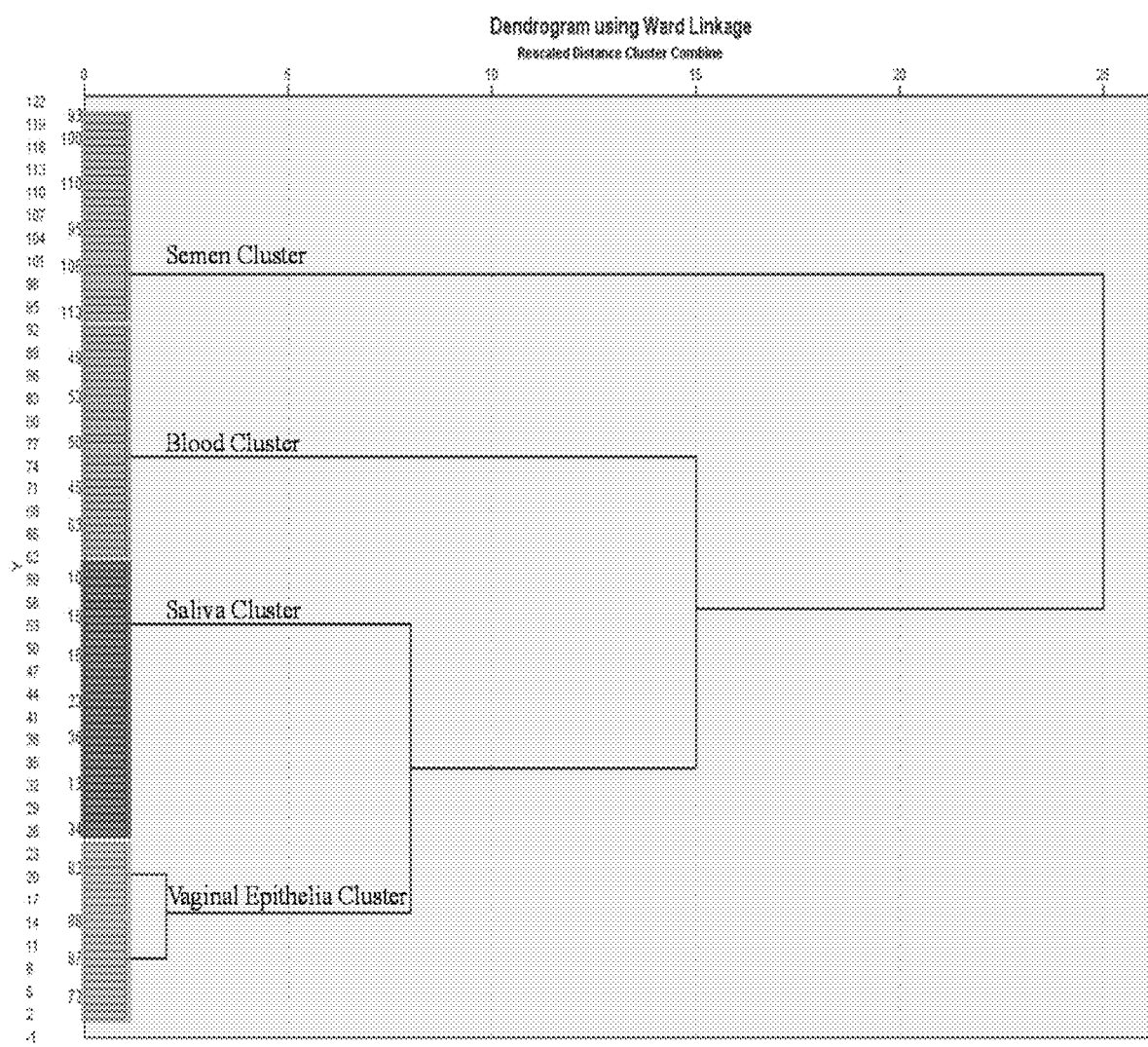
FIG. 9 provides a dendrogram resulting from cluster analysis of data from five most discriminatory CpGs. Each sample of a body fluid was correctly clustered together.

Inhibition Study: DNA samples received 0.08 mM of hematin and 0.24 mg/mL of humic acid either before or after bisulfite conversion to observe the effects of inhibition (FIGS. 7A-7C).

Degradation Study: DNA samples were subjected to 95° C. for 10-25 minutes to simulate fragmentation of DNA (FIGS. 8A-8D).

Example 3—Cluster Analysis to Identify the Optimal Combination of CpG Positions for Body Fluid Identification Cluster analysis of all 18 CpGs from the four source specific loci was performed to identify a cluster (combination) of CpGs that would accurately identify a source of DNA. Out of the 18 CpGs, methylation status information of only 5 CpGs is sufficient to correctly identify a source of DNA as buccal epithelial cell, blood, vaginal epithelial cells, or sperm.

TABLE 1

Population study ANOVA
ANOVA

| | | Sum of Squares | df | Mean Square | F | Sig. |
|---|---|---|---|---|---|---|
| BCAS4_CpG1 | Between Groups | 62208.648 | 3 | 20736.216 | 252.411 | .000 |
| | Within Groups | 9529.718 | 116 | 82.153 | | |
| | Total | 71738.367 | 119 | | | |
| CG06379435_CpG1 | Between Groups | 7995.915 | 3 | 2665.305 | 156.649 | .000 |
| | Within Groups | 1973.677 | 116 | 17.014 | | |
| | Total | 9969.592 | 119 | | | |

TABLE 1-continued

Population study ANOVA
ANOVA

| | | Sum of Squares | df | Mean Square | F | Sig. |
|---|---|---|---|---|---|---|
| CG06379435_CpG2 | Between Groups | 8502.360 | 3 | 2834.120 | 154.257 | .000 |
| | Within Groups | 2131.231 | 116 | 18.373 | | |
| | Total | 10633.592 | 119 | | | |
| VE_8_CpG3 | Between Groups | 43335.824 | 3 | 14445.275 | 234.960 | .000 |
| | Within Groups | 7131.642 | 116 | 61.480 | | |
| | Total | 50467.467 | 119 | | | |
| ZC3H12D_CpG2 | Between Groups | 83773.658 | 3 | 27924.553 | 494.730 | .000 |
| | Within Groups | 6547.508 | 116 | 56.444 | | |
| | Total | 90321.167 | 119 | | | |

Results of Tukey test show that each CpG is capable of differentiating its respective cluster to the exclusion of all other clusters (Table 2).

TABLE 2

Tukey's Honest Significant Difference test results for the five most discriminating CpGs of the body fluid multiplex. With p-value below 0.005 for each comparison, the body fluid multiplex correctly identifies the source as saliva, blood, vaginal epithelial cells, or sperm.

| Tukey Test | | | | | | 95% Confidence Interval | |
|---|---|---|---|---|---|---|---|
| CpG | Identified Cluster (I) | Other Clusters (J) | Mean Difference (I − J) | Std. Error | p value | Lower Bound | Upper Bound |
| BCAS4_CpG1 CpG at position 64 of SEQ ID NO: 16 | Saliva | Blood | 49.47 | 2.207 | <0.005 | 43.72 | 55.22 |
| | | Vaginal Epithelia | 23.655 | 2.376 | <0.005 | 17.46 | 29.85 |
| | | Semen | 54.048 | 2.27 | <0.005 | 48.13 | 59.97 |
| CG06379435_CpG1 CpG at position 129 of SEQ ID NO: 11 | Blood | Saliva | 18.913 | 1.004 | <0.005 | 16.29 | 21.53 |
| | | Vaginal Epithelia | 18.837 | 1.122 | <0.005 | 15.91 | 21.76 |
| | | Semen | 18.093 | 1.075 | <0.005 | 15.29 | 20.9 |
| CG06379435_CpG2 CpG at position 138 of SEQ ID NO: 11 | Blood | Saliva | 19.336 | 1.044 | <0.005 | 16.62 | 22.06 |
| | | Vaginal Epithelia | 19.07 | 1.165 | <0.005 | 16.03 | 22.11 |
| | | Semen | 19.225 | 1.192 | <0.005 | 16.31 | 22.14 |
| VE_8_CpG3 CpG at position 87 of SEQ ID NO: 1 | Vaginal Epithelia | Saliva | −42.534 | 2.055 | <0.005 | −47.89 | −37.18 |
| | | Blood | −48.589 | 2.132 | <0.005 | −54.15 | −43.03 |
| | | Semen | −50.643 | 2.181 | <0.005 | −56.33 | −44.96 |
| ZC3H12D_CpG2 CpG at position 45 of SEQ ID NO: 6 | Semen | Saliva | −56.896 | 1.882 | <0.005 | −61.8 | −51.99 |
| | | Blood | −69.475 | 1.959 | <0.005 | −74.58 | −64.37 |
| | | Vaginal Epithelia | −57.488 | 2.09 | <0.005 | −62.94 | −52.04 |

Accordingly, certain embodiments of the invention provide methods of identifying a sample as containing, or not containing, a cell selected from a vaginal epithelial cell, a sperm, a blood cell, or a buccal epithelial cell, the method comprising the steps of:
 a) determining the level of methylation at one or more of: CpG position 64 of SEQ ID NO: 16, CpG position 129 of SEQ ID NO: 11, CpG position 138 of SEQ ID NO: 11, CpG position 87 of SEQ ID NO: 1, and CpG position 45 of SEQ ID NO: 6, in:
  i) a genomic DNA isolated from the sample, and
  ii) optionally, a control genomic DNA;
 b) optionally, obtaining one or more reference values corresponding to the levels of methylation at the CpG positions listed in (a); and
 c) identifying the sample as containing or not containing a cell selected from a vaginal epithelial cell, a sperm, a blood cell, or a buccal epithelial cell based on the level of methylation at one or more of the CpG positions listed in (a).

In preferred embodiments, a sample is identified as containing or not containing a cell selected from a vaginal epithelial cell, a sperm, a blood cell, or a buccal epithelial cell based on the level of methylation at all the CpG positions: CpG position 64 of SEQ ID NO: 16, CpG position 129 of SEQ ID NO: 11, CpG position 138 of SEQ ID NO: 11, CpG position 87 of SEQ ID NO: 1, and CpG position 45 of SEQ ID NO: 6.

In further preferred embodiments, the sample is suspected to contain a vaginal epithelial cell, buccal epithelial cell, sperm, or blood cell isolated from a forensic sample.

Additional aspects of the methods discussed in this disclosure, such as preparation of samples, isolation of cells, isolation of genomic DNA, PCR amplification, design of primers, and/or sequencing to determine the methylation level at a CpG position are also application to the methods of determining methylation level at the five specific CpG positions listed here and such embodiments are within the purview of the invention.

We claim:

1. A method for identifying a sample as containing or not containing one or more human cells selected from a vaginal epithelial cell, a sperm, a blood cell, and a buccal epithelial cell, the method comprising the steps of:
   a) isolating a genomic DNA from the sample and optionally, from a control sample;
   b) treating the isolated genomic DNA from the sample and, optionally, from a control sample, with bisulfite;
   c) PCR amplifying four genetic loci, wherein the four genetic loci comprise the sequences of SEQ ID NOs: 1, 6, 11, and 16, respectively, in the bisulfite treated genomic DNA of b) to produce corresponding amplicons;
   d) sequencing the corresponding amplicons;
   e) determining a level of methylation at each of the four genetic loci based on the sequences of the corresponding amplicons,
   wherein determining the level of methylation at the genetic locus having the sequence of SEQ ID NO: 16 comprises determining the level of methylation at positions 64, 69, 81 and 88;
   f) obtaining each reference value corresponding to the level of methylation at the four genetic loci; and
   g) identifying the sample as:
      i) containing, or not containing, the vaginal epithelial cell by comparing the level of methylation at the genetic locus having the sequence of SEQ ID NO: 1 in the genomic DNA isolated from the sample to the reference value corresponding to the level of methylation at the genetic locus having the sequence of SEQ ID NO: 1,
      ii) containing, or not containing, the sperm by comparing the level of methylation at the genetic locus having the sequence of SEQ ID NO: 6 in the genomic DNA isolated from the sample to the reference value corresponding to the level of methylation at the genetic locus having the sequence of SEQ ID NO: 6,
      iii) containing, or not containing, the blood cell by comparing the level of methylation at the genetic locus having the sequence of SEQ ID NO: 11 in the genomic DNA isolated from the sample to the reference value corresponding to the level of methylation at the genetic locus having the sequence of SEQ ID NO: 11, and
      iv) containing, or not containing, the buccal epithelial cell by comparing the level of methylation at positions 64, 69, 81 and 88 of the genetic locus having the sequence of SEQ ID NO: 16 in the genomic DNA isolated from the sample to the reference value corresponding to the level of methylation at positions 64, 69, 81 and 88 of the genetic locus having the sequence of SEQ ID NO: 16.

2. The method of claim 1, wherein the sample is processed to separate a cell suspected to be a vaginal epithelial cell, sperm, blood cell, or buccal epithelial cell before the step of isolating the genomic DNA.

3. The method of claim 1, wherein the sample consists of vaginal epithelial cells, sperms, blood cells, buccal epithelial cells, or a combination thereof.

4. The method of claim 1,
   wherein the PCR amplifying is performed using primer pairs selected from:
      i) SEQ ID NOs: 2 and 3,
      ii) SEQ ID NOs: 7 and 8,
      iii) SEQ ID NOs: 12 and 13, and
      iv) SEQ ID NOs: 17 and 18,
   wherein each of the corresponding amplicons independently comprises the sequence of SEQ ID NO: 25, 26, 27 or 28 when SEQ ID NOs: 1, 6, 11, or 16 is 0% methylated.

5. The method of claim 1, wherein sequencing the amplicons is performed by a sequencing primer, wherein the sequencing primer is designed based on the sequences of SEQ ID NO: 1, 6, 11, or 16 and/or the sequences of the regions flanking the genetic locus having the sequence of SEQ ID NO: 1, 6, 11, or 16.

6. The method of claim 1, wherein the sequencing is performed by pyrosequencing.

7. The method of claim 5, wherein the sequencing primer for sequencing the amplicon is SEQ ID NO: 21, 22, 23, or 24.

8. The method of claim 4, wherein PCR amplification with the primer pairs is performed in one reaction.

9. The method of claim 1, wherein the step e) comprises determining the level of methylation at CpG position 87 of SEQ ID NO: 1, CpG position 45 of SEQ ID NO: 6, CpG position 138 of SEQ ID NO: 11, and CpG positions 64, 69, 81 and 88 of SEQ ID NO: 16.

10. The method of claim 1, wherein the step e) comprises determining the level of methylation at CpG position 87 of SEQ ID NO: 1, CpG position 45 of SEQ ID NO: 6, CpG position 129 of SEQ D NO: 11, CpG position 138 of SEQ ID NO: 11, and CpG positions 64, 69, 81 and 88 of SEQ ID NO: 16.

11. The method of claim 1, wherein the step e) comprises determining the level of methylation at CpG positions selected from CpG position 87 of SEQ ID NO: 1, CpG position 45 of SEQ ID NO: 6, CpG position 129 of SEQ ID NO: 11, and CpG positions 64, 69, 81 and 88 of SEQ ID NO: 16.

12. A method for determining the level of methylation at four genetic loci, wherein the four genetic loci comprise the sequences of SEQ ID NO: 1, 6, 11, and 16, respectively, in a genomic DNA isolated from a human cell, the method comprising a sequencing analysis that comprises:
   a) isolating the genomic DNA from the human cell;
   b) treating the isolated genomic DNA with bisulfate;
   c) PCR amplifying the four genetic loci to produce the corresponding amplicons, wherein the PCR amplifying is performed using primer pairs selected from
      i) SEQ ID NOs: 2 and 3,
      ii) SEQ ID NOs: 7 and 8,
      iii) SEQ ID NOs: 12 and 13, and
      iv) SEQ ID NOs: 17 and 18; and
   d) determining the sequences of the amplicons to determine the level of methylation;

wherein determining the methylation at the genetic locus having the sequence of SEQ ID NO: 16 comprises determining the methylation at positions 64, 69, 81 and 88.

13. The method of claim 12, wherein the cell is suspected to be a vaginal epithelial cell, sperm, blood cell, or buccal epithelial cell.

14. The method of claim 12, wherein the sequencing analysis is performed by pyrosequencing.

15. The method of claim 12, wherein the sequencing analysis of the amplicons is performed by one or more sequencing primers, wherein the sequencing primers are designed based on the sequences of SEQ ID NO: 1, 6, 11, and 16 and/or the sequences of the regions flanking the four genetic loci.

16. The method of claim 15, wherein the sequencing primer for sequencing the amplicon is SEQ ID NO: 21, 22, 23, or 24.

17. The method of claim 12, wherein PCR amplifying with the primer pairs is performed in one reaction.

18. A method for identifying a sample as containing or not containing one or more human cells selected from a vaginal epithelial cell, a sperm, a blood cell, and a buccal epithelial cell, the method comprising the steps of:
    a) determining a level of methylation at four genetic loci, wherein the four genetic loci comprise the sequence of SEQ ID NO: 1, 6, 11, and 16, respectively, in:
        i) a genomic DNA from the sample, and
        ii) optionally, a control genomic DNA,
    using primer pairs selected from
        i) SEQ ID NOs: 2 and 3,
        ii) SEQ ID NOs: 7 and 8,
        iii) SEQ ID NOs: 12 and 13, and
        iv) SEQ ID NOs: 17 and 18;
    b) optionally, obtaining each reference value corresponding to the levels of methylation at the four genetic loci; and
    c) applying cluster analysis to the determined levels of methylation and identifying the sample as:
        i) containing, or not containing, the vaginal epithelial cell based on the level of methylation at the genetic locus having the sequence of SEQ ID NO: 1, 6, 11, or 16 in the genomic DNA isolated from the sample falling within or outside of a vaginal epithelial cluster,
        ii) containing, or not containing, the sperm based on the level of methylation at the genetic locus having the sequence of SEQ ID NO: 1, 6, 11, or 16 in the genomic DNA isolated from the sample falling within or outside of a semen cluster,
        iii) containing, or not containing, the blood cell based on the level of methylation at the genetic locus having the sequence of SEQ ID NO: 1, 6, 11, or 16 in the genomic DNA isolated from the sample falling within or outside of a blood cluster, and/or
        iv) containing, or not containing, the buccal epithelial cell based on the level of methylation at the genetic locus having the sequence of SEQ ID NO: 1, 6, 11, or 16 in the genomic DNA isolated from the sample falling within or outside of a saliva cluster,
wherein determining the methylation at the genetic locus having the sequence of SEQ ID NO: 16 comprises determining the methylation at positions 64, 69, 81 and 88.

* * * * *